(12) United States Patent
Chiu et al.

(10) Patent No.: US 11,027,060 B2
(45) Date of Patent: Jun. 8, 2021

(54) FLEXIBLE TUBING, CANNULA AND INSERTION NEEDLE

(71) Applicant: Medtronic MiniMed, Inc., Northridge, CA (US)

(72) Inventors: Chia-Hung Chiu, Pasadena, CA (US); Hsifu Wang, Northridge, CA (US); Rebecca K. Gottlieb, Culver City, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 178 days.

(21) Appl. No.: 15/973,465

(22) Filed: May 7, 2018

(65) Prior Publication Data
US 2018/0318549 A1    Nov. 8, 2018

Related U.S. Application Data

(60) Provisional application No. 62/503,274, filed on May 8, 2017.

(51) Int. Cl.
| | |
|---|---|
| *A61M 5/158* | (2006.01) |
| *A61M 25/00* | (2006.01) |
| *A61L 29/06* | (2006.01) |
| *A61M 39/02* | (2006.01) |
| *A61M 5/142* | (2006.01) |

(Continued)

(52) U.S. Cl.
CPC ........... *A61M 5/158* (2013.01); *A61L 29/041* (2013.01); *A61L 29/06* (2013.01); *A61M 5/142* (2013.01); *A61M 5/14248* (2013.01); *A61M 25/0009* (2013.01); *A61M 25/0043* (2013.01); *A61M 39/02* (2013.01); *A61M 39/08* (2013.01); *A61B 17/3415* (2013.01); *A61B 2017/3454* (2013.01); *A61M 25/065* (2013.01);

(Continued)

(58) Field of Classification Search
CPC .. A61M 2005/1585; A61M 2005/1587; A61M 5/158; A61M 25/0662; A61M 25/0681; A61M 2025/0687

See application file for complete search history.

(56) References Cited

U.S. PATENT DOCUMENTS

| | | | |
|---|---|---|---|
| 4,755,173 A | 7/1988 | Konopka et al. | |
| 5,071,408 A * | 12/1991 | Ahmed | A61M 39/0208 606/108 |

(Continued)

OTHER PUBLICATIONS

International Search Report and Written Opinion dated Oct. 24, 2018, from application No. PCT/US2018/031455.

(Continued)

*Primary Examiner* — Emily L Schmidt
(74) *Attorney, Agent, or Firm* — Foley & Lardner LLP

(57) ABSTRACT

A flexible, fluid flow tubing is configured to be kink resistant, and a medical device is configured with such kink resistant tubing. The tubing has a length L and a circular cross-section shape taken perpendicular to the length dimension. The tubing has an inside radius r and an outside radius R, wherein $L/R \geq 34.8$, and wherein $R/r \geq 1.5$. The tubing may be made of a polyether block amide (PEBA) or other thermoplastic elastomer (TPE). The tubing may be received in a channel of a hollow needle, wherein the needle is slideable in the axial dimension relative to the tubing, to selectively slide off of at least a portion of the tubing.

22 Claims, 11 Drawing Sheets

(51) Int. Cl.
*A61M 39/08* (2006.01)
*A61L 29/04* (2006.01)
*A61M 25/06* (2006.01)
*A61B 17/34* (2006.01)

(52) U.S. Cl.
CPC ............... *A61M 2005/1585* (2013.01); *A61M 2005/1587* (2013.01); *A61M 2025/0059* (2013.01)

(56) References Cited

U.S. PATENT DOCUMENTS

| | | | |
|---|---|---|---|
| 5,370,607 A * | 12/1994 | Memmen | A61F 9/00781 604/294 |
| 5,380,290 A * | 1/1995 | Makower | A61M 25/06 604/160 |
| 5,568,806 A | 10/1996 | Cheney et al. | |
| 5,586,553 A | 12/1996 | Halili et al. | |
| 5,951,521 A | 9/1999 | Mastrototaro et al. | |
| 5,954,643 A | 9/1999 | Vanantwerp et al. | |
| 6,949,084 B2 | 9/2005 | Marggi et al. | |
| 8,721,656 B2 * | 5/2014 | De Juan, Jr. | A61F 9/00736 606/108 |
| 9,381,112 B1 * | 7/2016 | Sponsell | A61F 9/0017 |
| 2007/0167970 A1 * | 7/2007 | Sonoda | A61M 5/329 606/185 |
| 2009/0048563 A1 | 2/2009 | Ethelfeld et al. | |
| 2009/0076451 A1 | 3/2009 | Teisen-Simony et al. | |
| 2015/0217102 A1 | 8/2015 | Bourgeois et al. | |
| 2016/0074217 A1 | 3/2016 | Price et al. | |
| 2019/0117256 A1 * | 4/2019 | Jager | A61B 5/14865 |

OTHER PUBLICATIONS

International Preliminary Report on Patentability dated Nov. 21, 2019, from application No. PCT/US2018/031455.
Non-Final Office Action dated Oct. 13, 2020, from U.S. Appl. No. 15/973,471.
Notice of Allowance dated Feb. 19, 2021, from U.S. Appl. No. 15/973,471.

* cited by examiner

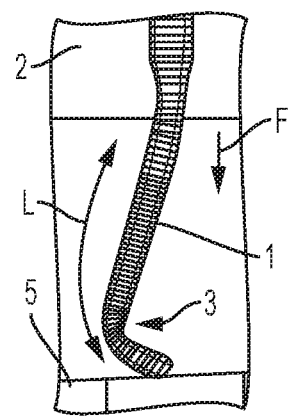
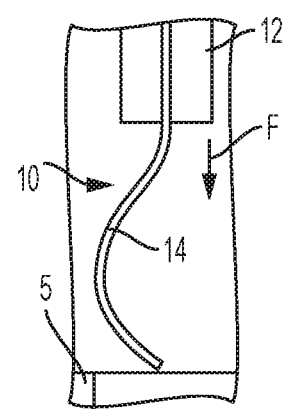
FIG. 1
PRIOR ART
FIG. 4
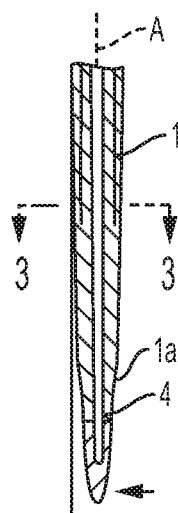
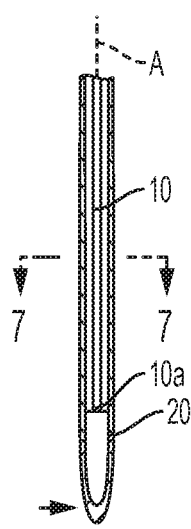
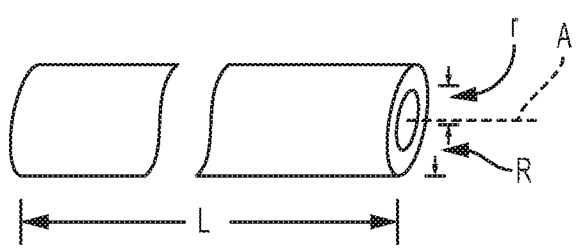
FIG. 5
FIG. 2
PRIOR ART
FIG. 6
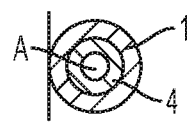
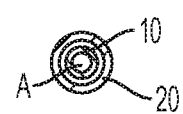
FIG. 3
PRIOR ART
FIG. 7
FIG. 8

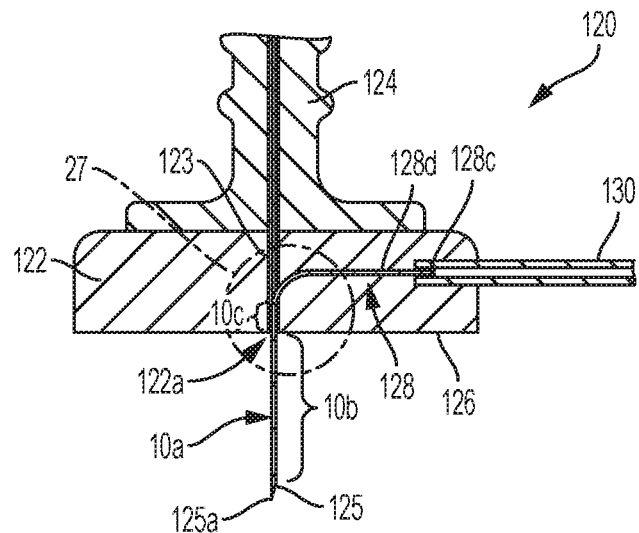
FIG. 26
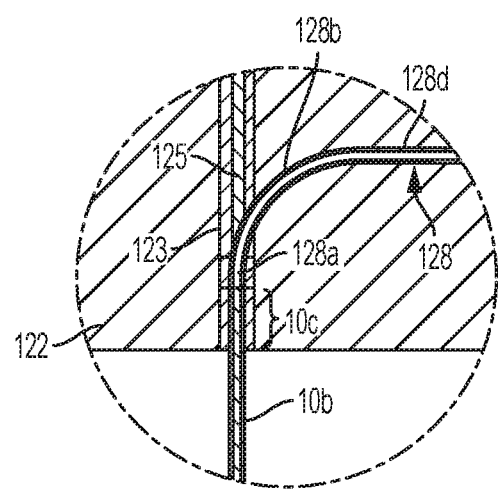
FIG. 27
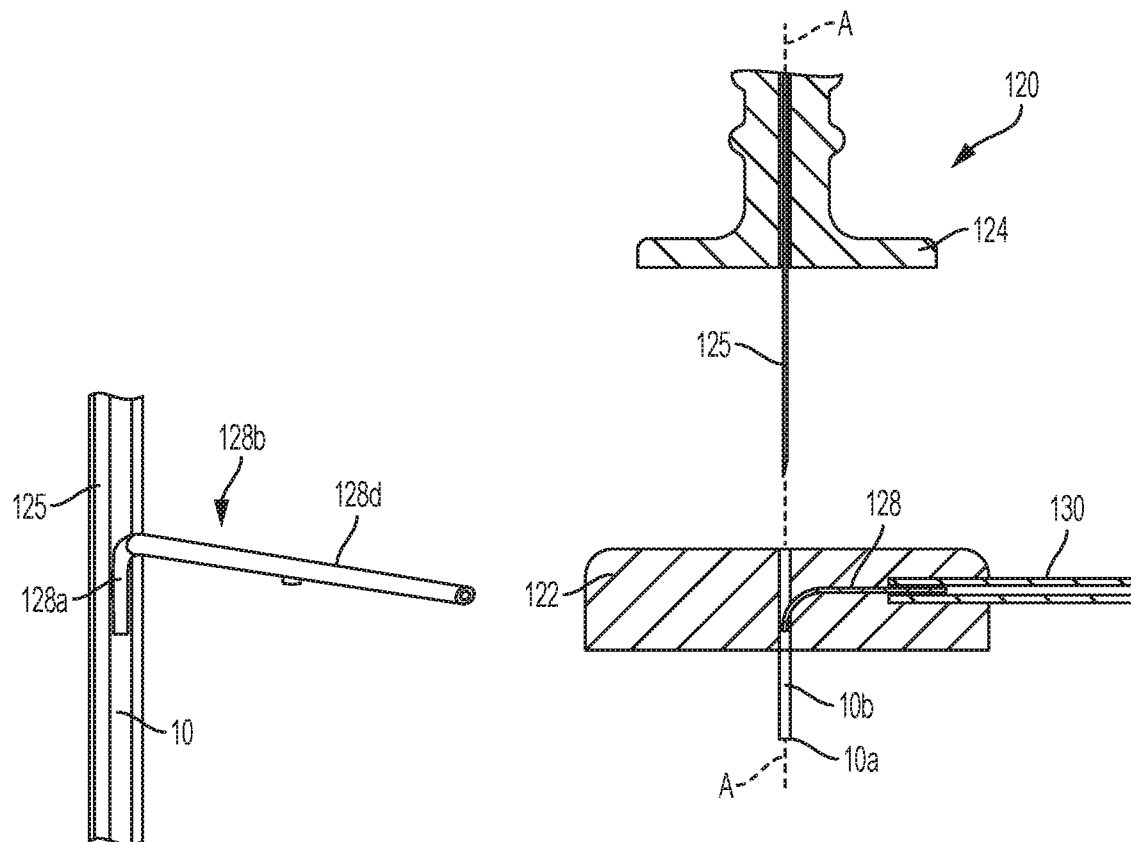
FIG. 28
FIG. 29

FLEXIBLE TUBING, CANNULA AND INSERTION NEEDLE

CROSS-REFERENCE TO RELATED PATENT APPLICATIONS

This application claims priority from Provisional U.S. Application 62/503,274, filed May 8, 2017, which is incorporated herein by reference in its entirety.

BACKGROUND

A flexible tubing for conveying fluid media and medical devices and systems that include such flexible tubing are described, where the flexible tubing is configured with a relatively small outer diameter, a relatively high degree of flexibility and a relatively high resistance to kinking or buckling. In certain examples, the flexible tubing forms a cannula and is received inside of a central channel of an insertion needle, for insertion into a patient, septum or other structure. In certain examples, a medical device includes the flexible tubing or the insertion needle, or both.

Various types of modern medical devices include or employ flexible tubing for conveying fluid media through a flow passage in the tubing. Such flexible tubing may be employed for conveying fluid media to or from a patient, a sensor, a pump, an insertion set or other medical device, a reservoir or fluid container, an implanted or partially implanted device, or the like. Such flexible tubing may be included in a sensor, a pump, in insertion set or other medical device. In addition, flexible tubing may be employed for forming a cannula configured to be inserted into or partially into a patient, for example, through the patient's skin.

Certain diseases or conditions may be treated, according to modern medical techniques, by delivering a medication or other substance to the body of a user, through a cannula or other tubing, either in a continuous manner or at particular times or time intervals within an overall time period. For example, diabetes is commonly treated by delivering defined amounts of insulin to the user at appropriate times. Some common modes of providing insulin therapy to a user include delivery of insulin through manually operated syringes and insulin pens. Other modern systems employ programmable fluid infusion devices (e.g., insulin pumps) to deliver controlled amounts of insulin to a user. In certain instances, these fluid infusion devices employ an insertion set, such as an infusion set, to be coupled to the body of a user for the delivery of the insulin. Typically, the infusion set includes a portion of a cannula that can be, for example, inserted under the skin of the user to deliver controlled amounts of infusion media (e.g., insulin) to the user.

Alternatively or in addition, an insertion set with a cannula may be configured or employed as a sensor set, to couple a sensor to a body of the user. For example, a sensor set may be configured to monitor glucose levels with a sensor set, to measure glucose levels in blood or interstitial fluid.

In certain contexts of use, it may be desirable to employ tubing that is relatively highly flexible or bendable, such that the tubing may be curved or bent during use. During installation or use, forces may be applied to the tubing that cause it to curve or bend. However, as shown in demonstration diagram of FIG. 1, when a compressive force F is applied along a length L of typical conventional tubing 1, the tubing 1 can tend to buckle or kink at a bend location 3 of the tubing. In FIG. 1, the tubing 1 extends from a structure 2, such as a base of an infusion set or another medical device housing, to a surface S. When the force F is applied (for example, by moving the medical device housing toward the surface S, the tubing 1 is caused to bend and kink at a bend location 3. More specifically, at the bend location 3, the tubing wall has collapsed inward, resulting in a reduction in the width or diameter of the flow passage in the tubing. Such kinking or collapsing of the wall of the flexible tubing can limit or cut off fluid-flow through the flow passage, which can adversely affect the operation or function of the medical device or system employing the tubing.

To avoid kinking or collapsing during insertion or use of a flexible tubing cannula and to improve patient comfort during insertion, an insertion needle may be extended through the flexible tubing cannula, as shown in FIGS. 2 and 3. In FIGS. 2 and 3, the needle 4 extends through the flexible tubing cannula 1 and supports the flexible tubing from bending during insertion into a patient's skin, septum or other structure. FIG. 3 shows the flexible tubing cannula 1 and the needle 4, as viewed in the cross-section 3-3 of FIG. 2.

The needle 4 has an end 4a that extends out from a distal end of the flexible tubing cannula 1, for piercing the patient's skin (or septum or other structure), during insertion of the flexible tubing cannula 1. Once the needle end 4a and a portion of the length of the cannula 1 have been inserted into the patient's skin (or septum or other structure), the needle 4 may be withdrawn from the flexible tubing cannula 1, to leave the distal end of the flexible tubing cannula 1 in the patient (or through the septum or other structure). Accordingly, in FIGS. 2 and 4, the flexible tubing cannula 1 must have a sufficiently large width or diameter, to be arranged on the outside of the needle 4. As a representative example, certain infusion set cannulas 1 have an outside diameter corresponding to a gauge of 23G (or about 0.025-0.0255 in.), and certain insertion needles 4 have an outside diameter of a gauge of 27G or 28G (or about 0.014 in.-0.0165 in.). To help improve patient comfort during insertion, the distal end 1a of the cannula 1 may be formed with a taper, which can add to manufacturing steps and costs.

In certain contexts and applications of use, it may be desirable to reduce or minimize the size of the outer diameter of the flexible tubing, while still providing sufficient fluid flow capacity through the tubing. In addition, it may be desirable for the tubing to have a relatively high degree of flexibility, but also withstand kinking or buckling when bent or curved.

SUMMARY

One or more examples and aspects described herein relate to a kink resistant fluid flow tubing for a medical device. Other examples and aspects described herein relate to a medical device including the fluid flow tubing. Other examples and aspects described herein relate to a medical device including the fluid flow tubing and a hollow insertion needle having a channel in which the fluid flow tubing is received for insertion into a patient, septum or other structure.

According to an example, a fluid flow tubing for a medical device includes a tubing configured to resist kinking and has a length L extending along an axial dimension of the tubing, and a circular cross-section shape taken perpendicular to the length dimension. The tubing has an inside radius r and an outside radius R, wherein L/R is equal to or greater than 34.8.

In a further example of the above-described fluid flow tubing, the R/r is equal to or greater than 1.5 (or, in particular example, within a range of about 1.5 to about 1.8).

In a further example of the above-described fluid flow tubing, the L/R ratio is within the range of 34.889 to 78.667.

In a further example of the above-described fluid flow tubing, the tubing is made of a polyether block amide (PEBA) or other thermoplastic elastomer (TPE).

In a further example of the above-described fluid flow tubing, the tubing is made of a polyether block amide (PEBA) or other thermoplastic elastomer (TPE), the L/R is within the range of 34.889 to 78.667, and the R/r is equal to or greater 1.5.

In a further example of the above-described fluid flow tubing, the tubing, the tubing is made of PEBAX™.

In a further example of the above-described fluid flow tubing, the tubing is located in a channel of a hollow needle.

In a further example, a medical device has a fluid flow tubing as described above, and a needle having a channel extending from a distal end of the needle along at least a portion of a length of the needle. The fluid flow tubing is located within the channel of the needle and the needle is slideable in the axial dimension relative to the fluid flow tubing, to selectively slide off of at least a portion of the fluid flow tubing.

In a further example of the above-described medical device, the fluid flow tubing has a distal end located within the channel of the needle, and wherein the needle is slideable in the axial dimension relative to the fluid flow tubing, to selectively slide off of the distal end portion of the fluid flow tubing.

In a further example of the above-described medical device, the needle has a slot at the distal end of the needle. The slot is open to the channel to allow a distal end of the fluid flow tubing to pass through the slot, as the needle is slid at least partially off of the fluid flow tubing.

In a further example, a medical device includes the above-described fluid flow tubing and a needle having a channel. The fluid flow tubing is located within the channel of the needle and the needle is slideable in the axial dimension relative to the fluid flow tubing, to selectively slide off of at least a portion of the fluid flow tubing. The needle has a slot at a distal end of the needle. The slot is open to the channel to allow a distal end of the fluid flow tubing to extend through the slot as the needle is slid at least partially off of the fluid flow tubing. The slot extends from the distal end of the needle, along at least a portion of a length dimension of the needle.

In a further example of the above-described medical device, the slot extends from the distal end of the needle, along the entire length dimension of the needle.

In a further example of the above-described medical device, the needle has a "C" shaped cross-section shape taken perpendicular to the length dimension of the needle.

A method of making a medical device includes providing a kink resistant fluid flow tubing having a length L extending along an axial dimension of the tubing. The method further includes receiving the fluid flow tubing with a channel in a needle, the channel extending from a distal end of the needle along at least a portion of a length of the needle, wherein the needle is slideable in the axial dimension relative to the fluid flow tubing, to selectively slide off of at least a portion of the fluid flow tubing.

In a further example of the above-described method, the fluid flow tubing has an outside radius R, and wherein L/R is equal to or greater than 13.1.

In a further example of the above-described method, the fluid flow tubing has an inside radius r, and wherein R/r is equal to or greater than 1.8.

In a further example of the above-described method, the fluid flow tubing has an outside radius R, and wherein L/R is within the range of 13.1 to 19.7.

In a further example of the above-described method, providing a kink resistant fluid flow tubing includes forming a tubing of a polyether block amide (PEBA) or other thermoplastic elastomer (TPE).

In a further example of the above-described method, providing a kink resistant fluid flow tubing includes forming a tubing of PEBAX™.

In a further example, a medical device includes a hollow needle having a central channel, a distal end and an opening at the distal end. The medical device further includes a fluid flow tubing configured to resist kinking. The tubing has a length L extending along an axial dimension of the tubing, and a circular cross-section shape taken perpendicular to the length dimension. The tubing has an outside radius R, wherein L/R is equal to or greater than 13.1. The tubing has a distal end and a length portion located within the central channel of the hollow needle. The needle is slideable in the axial dimension relative to the tubing, to selectively slide off of at least the distal end of the tubing, and cause the distal end of the tubing to exit the channel through the opening at the distal end of the needle as the needle is slid at least partially off of the tubing.

BRIEF DESCRIPTION OF THE DRAWINGS

The above and other aspects and features of the present invention will become more apparent to those skilled in the art from the following detailed description of the example embodiments with reference to the accompanying drawings, in which:

FIG. 1 is a cross-section view of a PRIOR ART tubing having a kink or buckle.

FIG. 2 is a cross-section view of the PRIOR ART tubing of FIG. 1, on an insertion needle.

FIG. 3 is a cross-section view of the tubing and insertion needle taken at 3-3 of FIG. 2.

FIG. 4 is a cross-section view of a flexible tubing according to an example embodiment.

FIG. 5 is a perspective view of a length of a flexible tubing according to an example embodiment.

FIG. 6 is a cross-section view of the flexible tubing of FIG. 5, within an insertion needle.

FIG. 7 is a cross-section view of the tubing and insertion needle taken at 7-7 of FIG. 6.

FIG. 8 is a cross-section view of the tubing and insertion needle taken at 8-8 of FIG. 6.

FIG. 26 is a cross-section view of another example insertion set device in a first state.

FIG. 27 shows an enlarged view of a portion of FIG. 26 identified by the circle labeled 27 in FIG. 26.

FIG. 28 shows another enlarged view of features in FIG. 27.

FIG. 29 is a cross-section view the example insertion set device of FIG. 26, in a second state.

DETAILED DESCRIPTION

Figure 9:
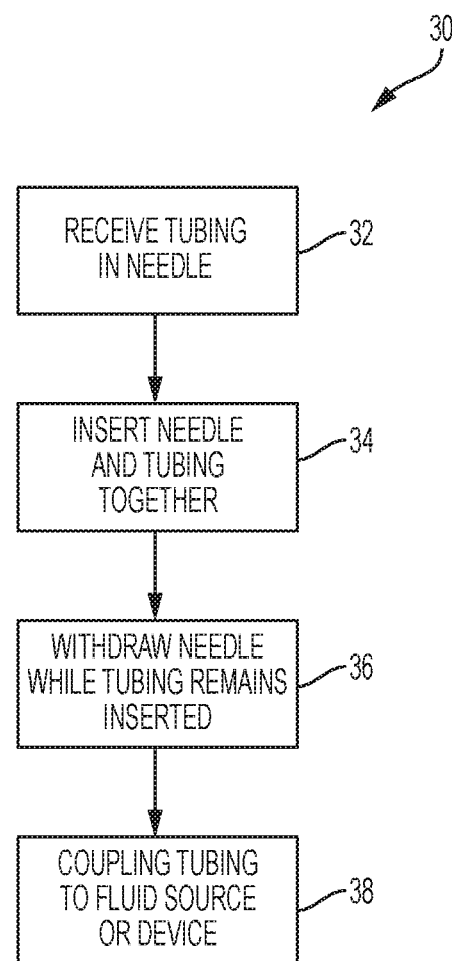
FIG. 9 is a flow chart of a method of using a tubing and insertion needle of FIG. 6.

Hereinafter, example embodiments will be described in more detail with reference to the accompanying drawings. The present invention, however, may be embodied in various different forms, and should not be construed as being limited to only the illustrated embodiments herein. Rather, these embodiments are provided as examples so that this disclosure will be thorough and complete, and will fully convey the aspects and features of the present invention to those skilled in the art. Accordingly, processes, elements, and techniques that are not necessary to those having ordinary skill in the art for a complete understanding of the aspects and features of the present invention may not be described. Unless otherwise noted, like reference numerals denote like elements throughout the attached drawings and the written description, and thus, descriptions thereof may not be repeated. Further, features or aspects within each example embodiment should typically be considered as available for other similar features or aspects in other example embodiments.

Certain terminology may be used in the following description for the purpose of reference only, and thus are not intended to be limiting. For example, terms such as "top", "bottom", "upper", "lower", "above", and "below" could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

It will be understood that when an element or feature is referred to as being "on," "connected to," or "coupled to" another element or layer, it can be directly on, connected to, or coupled to the other element or feature, or one or more intervening elements or features may be present. In addition, it will also be understood that when an element or features is referred to as being "between" two elements or features, it can be the only element or feature between the two elements or features, or one or more intervening elements or features may also be present.

The terminology used herein is for the purpose of describing particular embodiments and is not intended to be limiting of the present invention. As used herein, the singular forms "a" and "an" are intended to include the plural forms as well, unless the context clearly indicates otherwise. It will be further understood that the terms "comprises," "comprising," "includes," and "including," "has," "have," and "having," when used in this specification, specify the presence of the stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list.

As used herein, the term "substantially," "about," and similar terms are used as terms of approximation and not as terms of degree, and are intended to account for the inherent variations in measured or calculated values that would be recognized by those of ordinary skill in the art. Further, the use of "may" when describing embodiments of the present invention refers to "one or more embodiments of the present invention." As used herein, the terms "use," "using," and "used" may be considered synonymous with the terms "utilize," "utilizing," and "utilized," respectively.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and/or the present specification, and should not be interpreted in an idealized or overly formal sense, unless expressly so defined herein.

Various types of modern medical devices and cannulas include or employ flexible tubing for conveying fluid media. A flexible tubing for conveying fluid media and medical devices and systems that include such flexible tubing are described, where the flexible tubing is configured with a relatively small outer diameter, a relatively high degree of flexibility and a relatively high resistance to kinking or buckling. In certain examples, the flexible tubing forms a cannula configured to be inserted into or partially into a patient, such as, through the patient's skin. The flexible tubing cannula may be included in an insertion set or other medical device or system. Accordingly, in certain examples, a flexible tubing as described herein is included in an insertion set, an infusion set, a sensor device, an infusion pump or other fluid delivery system, or the like.

Also as described herein, a flexible tubing according to certain examples described herein may be configured to fit inside of a hollow needle, for insertion into a patient, septum or other structure. In contrast to prior arrangements in which a tubing is arranged on the outside of an insertion needle (as represented in FIGS. 2 and 3), a flexible tubing according to certain examples described herein may have a sufficiently small outer diameter, to fit within an open channel of an insertion needle.

Therefore, according to certain examples described herein, a flexible tubing is configured with a reduced or minimized outer diameter (relative to certain conventional medical tubing), while still providing sufficient fluid flow capacity through the tubing, a relatively high degree of flexibility, and a resistance to kinking or buckling when bent or curved. For example, a cannula formed from a thin, flexible tubing may have a reduced or minimized outer diameter and relatively high flexibility (without kinking or buckling) for improved patient comfort.

A relatively high degree of flexibility in the tubing, without kinking or buckling, can allow the tubing to bend and curve, which can improve the ability of the tubing to be configured, fitted or adjusted in a medical device or system. Also, a flexible tubing cannula having thin outer dimension and a relatively high degree of flexibility can improve patient comfort, by minimizing insertion trauma and allowing the cannula to flex with movement of the patient.

A flexible tubing for a medical device or system described herein may have an axial length dimension and a generally circular cross-section shape taken perpendicular to the axial length dimension, and a central passage through which fluid may flow. In other examples, the tubing may have a cross-section shape that is not a circle, such as, but not limited to an oval, another curved shape, a polygon or a shape having a combination of curved and straight edges. The cross-section shape of the central passage may have a circular or another shape, and may correspond to (be the same shape as) the outer cross-section shape of the tubing. In other examples, the cross-section shape of the central passage may be a different shape relative to the outer cross-section shape of the tubing.

The material of the flexible tubing is compatible with fluids intended to be conveyed through the tubing, and with other materials to which the tubing may come into contact or be connected, in the intended environment of use. In certain examples, the flexible tubing is made of a material that is biologically compatible, for use in contexts in which the flexible tubing is in contact or connected with a biological entity (such as a human patient or another biological entity), or is implanted fully or partially in the patient (or other biological entity). In certain examples, the flexible tubing is treated in one or more processes for enhancing biologically compatibility or other compatibility for an intended environment or use, such as, but not limited to cleaning, sterilizing, treating or coating with Heparin or other anticoagulant, an antibiotic, nitric-oxide or other materials, or the like.

In certain examples the tubing is made of a material that is suitable for medical uses, including but not limited to materials compatible with, and suitable for, implanting or partially implanting into a patient or other biological entity. Alternatively or in addition, the tubing material is selected to be compatible with and suitable for conveying one or more desired or predefined fluids (such as, but not limited to insulin, cancer or AIDs treatment drugs, or other medications, drugs or therapy fluids). Such materials may include, but are not limited to a polyether block amide (PEBA) of thermoplastic elastomer (TPE) such as PEBAX™, a polytetrafluoroethylene (PTFE), an ethylene tetrafluoroethylene (ETFE), a thermoplastic polyurethane (TPU) such as PELLETHAN™, or the like. However, for other contexts and applications of use, the tubing may be made of other materials suitable and compatible with those contexts and applications. The tubing may be made by any suitable manufacturing process including, but not limited to extrusion, molding, machining or the like.

An example of a flexible tubing 10 having a circular cross-section shape defining an axial dimension A, is shown in FIGS. 4 and 5. In FIG. 4, the flexible tubing 10 extends from or through a housing or other structure of a medical device 12, and has a length portion that is bent. In FIG. 5, a length L of the flexible tubing 10 is shown.

The flexible tubing 10 has a central channel or passage 14, through which fluid may flow. The fluid flow passage 14 extends along the length L of the tubing 10, and shares the same axis A of the tubing 10. As shown in FIG. 5, the tubing 10 has an outer peripheral surface 16, an inner surface (the outer surface of the fluid flow passage 14), and a thickness t between the outer peripheral surface 16 and the inner surface (outer surface of the fluid flow passage 14). The tubing 10 has an inner radius r (the radius of the fluid flow passage 14) and an outer radius R (the radius of the outer peripheral surface 16).

In certain examples, the flexible tubing 10 is configured to have a relatively high L/R length-to-outer-radius ratio (or slenderness ratio), to be sufficiently flexible and kink resistant. In certain examples, the ratio R/r (between the outer radius R and the inner radius r) is increased or maximized, to increase the flexibility of the tubing 10. In particular examples, the L/R is selected to be sufficiently high (in dimensions suitable for the context of use) to increase or maximize the kink resistance of the tubing, and also the ratio R/r is selected to be sufficiently high (in dimensions suitable for the context of use), to increase or maximize the flexibility of the tubing.

In addition to increasing or maximizing one or both of the ratios L/R and R/r of the tubing (in dimensions suitable for the context of use of the tubing), it may be beneficial for certain applications of use to reduce or minimize the outer radius R of the flexible tubing, while still allowing for sufficient fluid flow volume or pressure (or both). A thinner tubing may be able to fit into narrow spaces such as, but not limited to an inner passage of a hollow needle. A thinner tubing may provide a more comfortable cannula or other implantable or partially implantable device. Also, if the slenderness ratio L/R is too small, the tubing can have a tendency to kink or buckle along the length L.

Accordingly, in particular examples, a relatively thin tubing that is both flexible and resistant to kinking is configured of a PEBAX, PTFE, or other suitable material, and has an L/R ratio that is equal to or greater than 34.8. Alternatively or in addition, the tubing has an R/r ratio that is equal to or greater than 1.5. In particular examples, the L/R ratio is between about 34.889 and about 78.667. In particular examples, the R/r ratio is between about 1.5 and about 1.8.

A flexible tubing having such dimensions can have an improved flexibility and resistance to kinking or buckling, as compared to typical medical grade tubing and cannula tubing. In addition, a flexible tubing having such dimensions may be configured relatively thin, for example, with an outer radius of about 0.0045 inch (0.1143 mm) or less.

Thus, in certain examples, a tubing 10 made of a PEBA of other TPE such as PEBAX™, or a PTFE (or a combination of those materials) has an outer radius of about 0.1143 mm. (0.0045 inch) and, thus, has an inner radius of about 0.127 mm. (0.0025 inch) (applying the above-noted R/r ratio of 1.8), and a length (or length portion) L in the range of about 6 mm. to about 9 mm. (applying the above L/R ratio ranges), as shown in Table 1. In other examples, the outer radius is about 0.1143 mm. (0.0045 inch) and the inner radius is about 0.0762 mm. (0.003 inch) (applying the above-noted R/r ratio of 1.5), and a length (or length portion) L in the range of about 4 mm. to about 5 mm. (applying the above L/R ratio ranges), as shown in Table 1.

TABLE 1

| Length | R | r | L/R | R/r |
|---|---|---|---|---|
| 4 mm. (0.157 inch) | 0.1143 mm. (0.0045 inch) | 0.0762 mm. (0.003 inch) | 34.889 | 1.50 |
| 5 mm. (0.197 inch) | 0.1143 mm. (0.0045 inch) | 0.0762 mm. (0.003 inch) | 43.778 | 1.50 |
| 6 mm. (0.236 inch) | 0.1143 mm. (0.0045 inch) | 0.127 mm. (0.0025 inch) | 54.444 | 1.80 |
| 9 mm. (0.354 inch) | 0.1143 mm. (0.0045 inch) | 0.127 mm. (0.0025 inch) | 78.667 | 1.80 |

In the table 1 examples, the tubing 10 can be relatively flexible, while having a relatively high resistance to kinking or buckling (collapsing of the outer wall) when bent along a length portion of length L.

In addition, the flexible tubing 10 can be configured relatively thin (can have a relatively small outer diameter). By reducing or minimizing the size of the outer diameter of the flexible tubing 10, various advantages are available such as, but not limited to improving patient comfort, and reducing the size and the weight of a medical device or system that includes the tubing.

In certain examples as shown in FIGS. 6 and 7, the flexible tubing 10 is configured to be sufficiently thin, to extend through a central channel of a hollow insertion needle 20. FIG. 7 shows the flexible tubing and the insertion needle 20, as viewed in the cross-section 7-7 of FIG. 6. The insertion needle 20 has a hollow, central channel configured to receive the flexible tubing 10. When the flexible tubing 10 is received within the hollow channel of the insertion needle 20, the insertion needle 20 and flexible tubing 10 are moveable relative to each other in the axial direction A, for example, to allow the needle to slide off of the flexible tubing 10, or to allow the flexible tubing to slide out of the needle 30.

In particular examples, a cannula composed of the flexible tubing 10 can be received within the channel of the hollow needle 20, with the distal end 10a of the flexible tubing 10 located at least partially inside of the channel of the hollow needle 20 as shown in FIGS. 6 and 7. When the flexible tubing 10 is received in the channel, the needle 20 is slideable relative to the flexible tubing 10, in the axial direction. In that arrangement, the hollow needle 20 may be inserted into a patient's skin (or a septum or other structure), a sufficient distance to place the distal end of the flexible tubing 10 in the patient (or through the septum or other structure). The hollow needle 20 provides additional rigidity and can have a pointed or sharp tip, to assist in piercing the patient's skin (or septum or other structure) during insertion. Once the hollow needle 20 containing the flexible tubing 10 is inserted into (or partially into) the patient's skin (or a septum or other structure), the hollow needle 20 may be slid off of some or all of the flexible tubing 10, while leaving the distal end 10a of the flexible tubing 10 in place in the patient (or through the septum or other structure).

By locating a cannula composed of flexible tubing 10 inside of the hollow needle 20, various advantages are available such as, but not limited to reducing insertion force needed to insert the cannula and improving patient comfort. In addition, the distal end 10a of the flexible tubing 10 need not be tapered, which can help to reduce or minimize manufacturing costs as compared to tapered tubing. Also, a straight cylindrical tip, without taper, can more evenly distribute compression stresses compared to tubing configurations with a tapered distal end.

In the example of FIGS. 6 and 7, the distal end portion 20a of the needle 20 has a slot or opening along the axial dimension A of the side wall of the needle. Accordingly, the cross-section shape of the distal end portion 20a of the needle (at the cross-section 7-7 in FIG. 6) has a slotted circle or "C" shape, as shown in FIG. 7. The slot or opening in the side wall of the needle 20 extends from the distal end 20b of the needle 20, along at least a portion of the axial length of the needle 20. Accordingly, when the needle 20 is moved in the axial direction relative to the tubing 10, to slide off (or partially off) of the tubing 10, the distal end portion 20a of the needle 20 may be slid off of at least a portion of the tubing 10, leaving the distal end 10a of the tubing 10 outside of the needle 20.

In the example in FIG. 6, the slot or opening in the side wall of the needle 20 extends a portion, but not the entire axial length of the needle 20, such that a cross-section shape of the needle 20 at 8-8 in FIG. 6 has a shape as shown in FIG. 8, where that section of the needle has a fully cylindrical shape. In other examples, the slot or opening in the side wall of the needle 20 extends the entire axial length (or substantially the entire axial length) of the needle 20, such that a cross-section shape of the needle 20 is similar to that shown in FIG. 7, along the entire (or substantially the entire) axial length of the needle 20. In further examples, the hollow needle 20 may have a small opening or slot at its distal end (or sharp end) through which the distal end portion of the flexible tubing 10 may extend as the needle 20 is withdrawn, but has a full cylindrical shape (with a cross section shape as shown in FIG. 8) along the rest of the length of the needle.

An example process 30 of using a flexible tubing cannula is described with reference to FIG. 9. The process 30 includes receiving a tubing in a needle (at 32). The tubing may be received in a channel of a needle as described herein with respect to the flexible tubing 10 received within the central channel of the slotted needle 20.

The process 30 also includes inserting the needle and tubing (at 34). The needle and tubing may be inserted into a patient, septum or other structure, as described herein with respect to inserting the needle 20 while the tubing 10 is located within the central channel of the needle 20.

The process 30 also includes withdrawing the needle while the tubing is held in an inserted state (at 36). The needle may be slid off of the tubing as described herein with respect to sliding the needle 20 in the axial direction relative to the tubing 10.

The process 30 also includes coupling the tubing to a device, fluid source or a fluid receptacle (at 38). For example, the tubing may be coupled to a medical device, a fluid source or a fluid receptacle at any stage of the process 30. In certain examples, the tubing has a second end (or port) coupled to a fluid source, for receiving fluid to be conveyed through the tubing to a patient (or device to which the distal end of the tubing is connected). The fluid source may include, but is not limited to an infusion pump, fluid-containing reservoir, or other fluid delivery system. In other examples, the second end (or port) of the tubing may be coupled to a reservoir or volume for receiving fluid from the patient (or from the device to which the distal end of the tubing is connected). For example, the reservoir or volume may be a portion of a sensor that receives fluid from a patient (or from a device) and senses detectable parameters of the fluid.

In other examples, a flexible tubing 10 or a hollow needle 20 with a flexible tubing 10 may be employed in other suitable processes. In systems, devices and process in which the flexible tubing 10 is received within the central channel of the hollow needle 20 for insertion, various advantages may be available, including but not limited to an ability to minimize or reduce the outer diameter of the flexible tubing 10 (for example, relative to a tubing and inserter configuration of FIGS. 1-3, which can significantly improve patient comfort during insertion and use when the flexible tubing 10 forms a cannula. In addition, the flexible tubing 10 may have a single, constant diameter, which can reduce manufacturing costs and improve patient comfort. Also, stress on the flexible tubing 10 before and during insertion may be reduced or minimized (for example, relative to a tubing and inserter configuration of FIGS. 1-3 in which the tubing 1 is located on the outside of the inserter needle 4).

Further examples of slotted needle configurations, insertion sets and other medical devices that include or employ slotted needles are described with reference to FIGS. 10-32. The systems and devices in FIGS. 10-32 may include or employ a kink resistant, flexible tubing 10 as described herein with reference to FIGS. 4-8. However, other examples of such systems and devices may employ other suitable tubing or flexible tubing. The insertion sets may be infusion sets configured to couple to (or be part of) an infusion system for delivering a fluid media to a patient or other entity, through the flexible tubing, for example, from an infusion pump, reservoir or other delivery device. Alternatively or in addition, the insertion sets may be configured to couple to (or be part of) a sensor system for delivering a fluid media from a patient or another entity, through the flexible tubing, for example, to a sensing device. In other examples, the insertion sets may be configured to couple to (or be part of) other systems that deliver fluid media to or from a patient or another entity.

Figure 10:
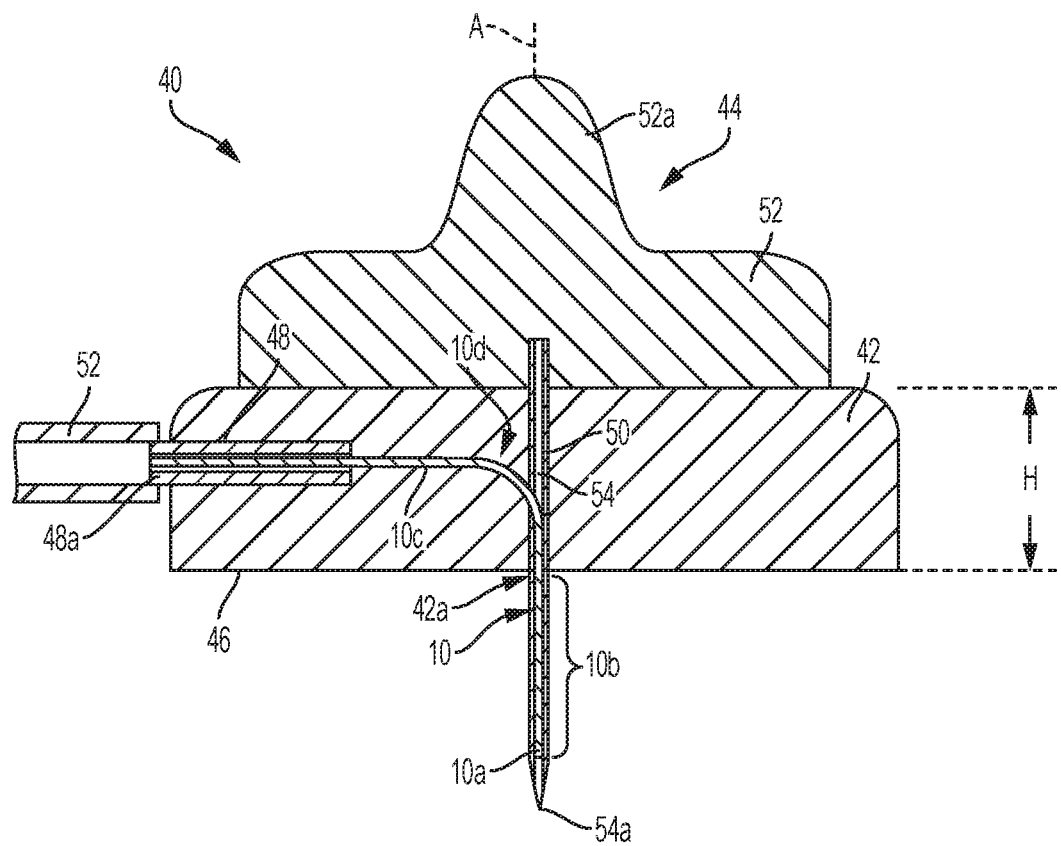
FIG. 10 is a cross-section view of an example insertion set device in a first state.
Figure 11:
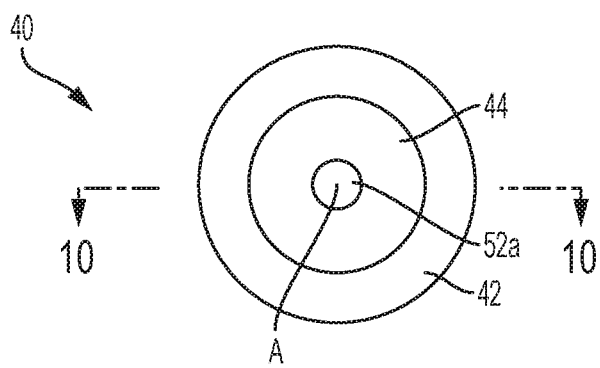
FIG. 11 is a top view of the example insertion set device of FIG. 10.
Figure 12:
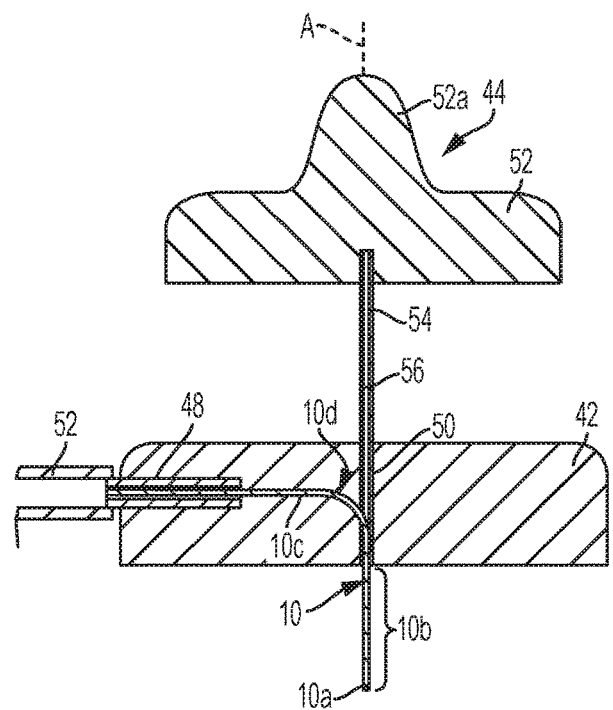
FIG. 12 is a further cross-section view of the example insertion set device of FIG. 10 transitioning to a second state.
Figure 13:
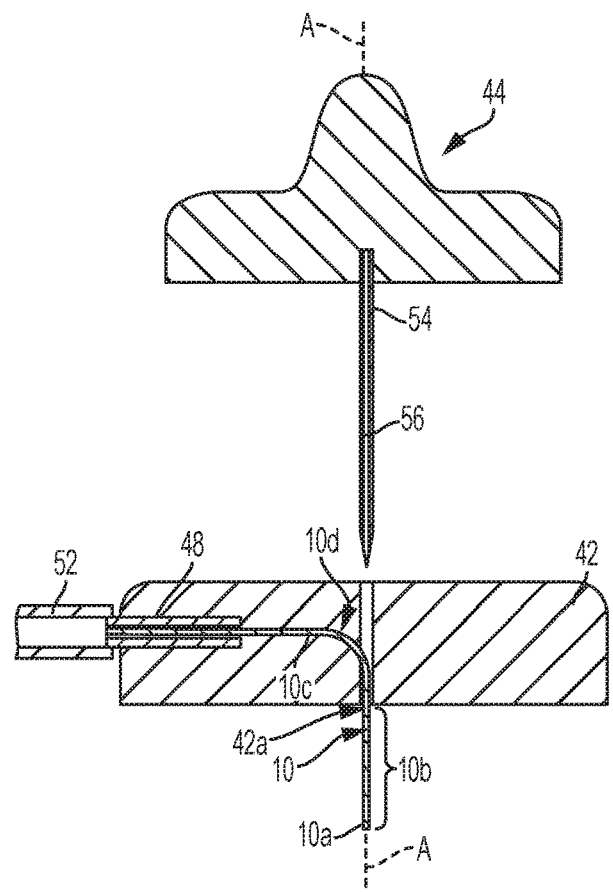
FIG. 13 is a further cross-section view of the example insertion set device of FIG. 10 in the second state.

An example of an insertion set device 40 having a cannula formed with or of a flexible tubing 10 (or other suitable tubing) is described with reference to FIGS. 10-14. FIGS. 10 and 11 show a cross-section side view and a top view, respectively, of the insertion set device 40, in a first state. The cross-section view in FIG. 10 is taken along 10-10 of FIG. 11. FIG. 12 shows a similar cross-section view of the insertion set device 40, transitioning from the first state to a second state. FIG. 13 shows a similar cross-section view of the insertion set device 40, in the second state.

The insertion set device 40 includes a base 42 and an inserter 44. In the first state, as shown in FIGS. 10 and 11, the inserter 44 is received and supported by the base 42, but is removable from the base 42 by moving the inserter 44 (e.g., lifting upward in FIG. 10) from the base 42 in the axial direction A (or otherwise moving the inserter 44 and base 42 apart in the axial direction A). In FIG. 12, the inserter 44 is partially lifted from the base 42. In the second state, as shown in FIG. 13, the inserter 44 is fully separated (fully lifted) from the base 42.

The base 42 has a surface 46 configured to abut against or secure to the skin of a patient, or to a surface of a septum or other device to which the cannula of flexible tubing 10 is to be inserted. In particular examples, one or more mechanisms for securing the surface 46 to the patient, septum or other device may be included on the base 42, such as, but not limited to adhesive on the surface 46, straps, suture tabs or openings, or the like.

Figure 14:
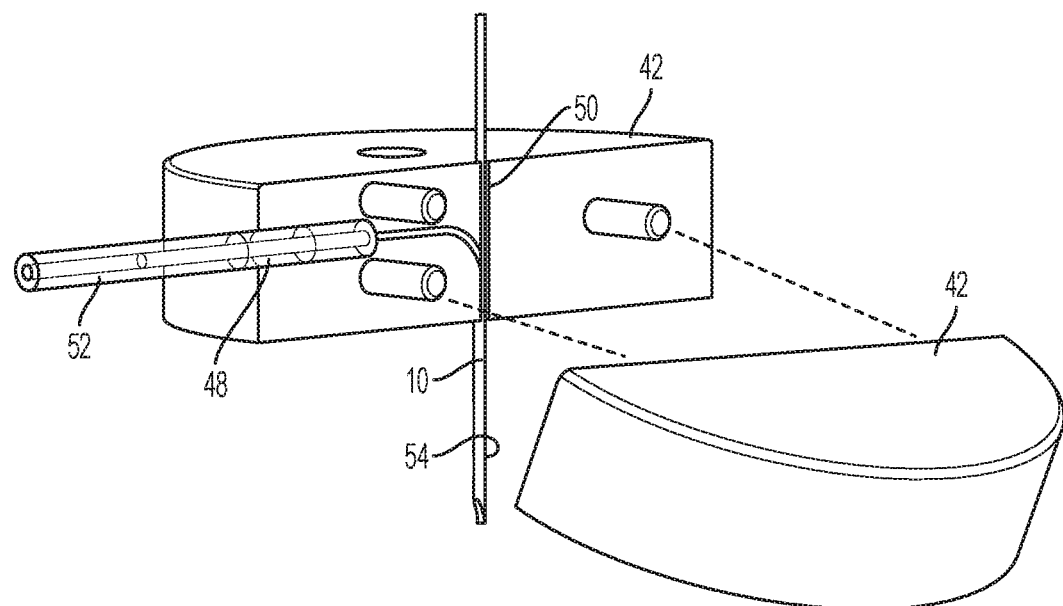
FIG. 14 is a partial exploded, perspective view of a base of the example insertion set device of FIG. 10.

The base 42 may include one or more parts that form a housing for holding or containing the flexible tubing 10 and a coupling 48. In the example of FIG. 14, the base 42 includes two parts that may be separated to allow access to internal components, and that couple together to form a disc-shaped housing that contains the internal components. Any suitable mechanism may be employed to couple the base parts together to form the housing of the base 42, including, but not limited to shaft protrusions 43 on one part that fit into corresponding apertures in another part, in a friction-fit manner. Alternatively or in addition, other suitable mechanism may be employed to couple the base parts together, including, but not limited to adhesives, screws or other threaded fasteners, friction fitted groove and rib configurations, or the like. In other examples, the base 42 may include a single part housing, or more than two parts that form a housing, the housing may have other suitable disc or non-disc shapes, and other suitable connection structures may be employed for connecting the housing parts. In yet other examples, the base 42 may have a be configured with a hollow or partially hollow interior, for example, in a clamshell configuration. In other examples, the base 42 may have other suitable configurations that holds and encloses a portion of the flexible tubing 10 and a portion of the coupling 48.

The base 42 shown in FIGS. 10-14 has a generally rounded disc shape, with a rounded top edge. However, in other examples, the base 42 may have other suitable shapes. The base 42 may be made of any suitable material, such as, but not limited to plastic, metal, ceramic, composite material, or the like. In particular examples, the base 42 is a generally rigid structure. In other examples, the base 42 may have sufficient rigidity to hold its shape, but may be made of material having some flexibility or malleability, such as but not limited to a soft plastic, a rubber or rubber-like material, or the like.

The base 42 has a first opening 42a in the surface 46 (the bottom surface in FIGS. 10-14) and includes a needle passage 50 extending from the first opening 42a, to a second opening 42b in a surface of the base 42 (the top surface in FIGS. 10-14) opposite to the surface 46. The passage 50 may be formed as a channel or bore through the material of the base 42 as shown in FIG. 14. In further examples, the passage 50 may be the interior channel of a tube-like structure in the base 42, extending between the first and second openings 42a and 42b.

The distal length portion 10b of the tubing 10 extends out from the first opening 42a in the surface 46 of the base 42, such that the distal end 10a of the tubing 10 is located outside of the base 42. A further length portion 10c of the tubing 10 is located within the base 42 and extends from the distal length portion 10b, to the coupling 48. The further length portion 10c has a tubing end that is connected in fluid flow communication with the coupling 48.

The further length portion 10c of the flexible tubing 10 has a first section that extends along part of the length of the passage 50, a second section that forms a relatively sharp bend 10d and a third section that extends from the bend 10d to the coupling 48. The bend 10d may form a relatively sharp angle, such that the height H in the axial dimension of the base 42 (dimension between the surface 46 and the opposite facing surface) may be made relatively small or minimized. In certain examples, the bend 10d may be about 90°, such that the coupling 48 is directed about 90° from the direction of distal length portion 10b of the tubing 10. This arrangement allows a further tubing 52 to be connected to the coupling 48, external to the base 42, and extend outward from the base 42 in a direction substantially parallel to and along the surface of the patient's skin (or other surface) to which the base 42 secures. Accordingly, the base 42 and tubing 52 may be more easily concealed under clothing or the like. In other examples, the bend 10d may be between about 90° and about 160° (or, in particular examples, between about 135° and about 160°) relative to the axial dimension A.

In certain system examples, the further tubing 52 may be connected or configured to connect (at an end opposite to the end connected to the coupling 48) to an infusion pump or other fluid delivery device, a sensor or monitoring device, or the like. In certain examples, the further tubing 52 may have a tubing configuration as described herein with reference to the flexible tubing 10. In other examples, the further tubing 52 may be another type of flexible tubing, a non-flexible tubing, or a combination of flexible and non-flexible tubing lengths.

The coupling 48 may be any suitable fluid coupling structure, for coupling two tubing ends together, for fluid flow communication. In particular examples, the coupling 48 allows for connection and disconnection of further tubing to the base 42. In the examples of FIGS. 10-14, the coupling 48 may include an in-line tubular structure having a central passage with an inside diameter large enough to receive an end length portion of the third section of the tubing portion 10c. The coupling 48 has an end portion 48a located outside of the base 42, for securing to the further tubing 52. In the example in FIGS. 10-14, further tubing 52 has an inside diameter large enough to receive some or all of the end portion 48a of the coupling 48. In other examples, the end portion 48a of the coupling 48 has an inside diameter large enough to receive an end length portion of the further tubing 52 within the coupling 48. The end length portion of the tubing portion 10c may be fixed and sealed to the coupling 48, and the tubing 52 may be fixed and sealed to the coupling 48 by any suitable mechanism, including friction fitting, adhesives, welds, or the like. In other examples, the coupling 48 may be another suitable in-line coupling device, such as, but not limited to a Luer Lok™ device, Luer™-slip device, slip tip device, hollow needle and septum configuration or the like.

In the example of FIGS. 12 and 13, the coupling 48 or the third section of the tubing (or both) are secured and fixed to the base 42. In further examples, additional structure (not shown) may be included in the base 42, to secure the coupling 48 and the tubing 10 to the base, in a fixed relation. However, the distal length portion 10b of the flexible tubing 10 is sufficiently flexible to flex and bend along the distal length portion 10b. In contexts in which the distal length portion 10b forms a cannula for insertion into a patient's skin, the flexibility of the distal length portion 10b can provide additional comfort to the patient, by allowing the cannula to move and flex with the patient's skin.

As discussed above, the inserter 44 is received and supported by the base 42, but is selectively removable from the base 42. The inserter 44 includes an inserter body 53 and a slotted inserter needle 54. The inserter body 53 may have a handle portion 53a configured to be easily gripped by a human hand. The handle portion 53a may include one or more surfaces with ribs or other contour features, an added friction material, or the like, for enhancing frictional engagement and gripping by a user, tool or machine. In certain examples, the inserter body 53 may include a handle 53a or other portion configured to be gripped or otherwise secured to a separate tool or device, such as an inserter device (not shown) for installing (inserting) the insertion set device 40 in a patient or other entity.

Figure 15:
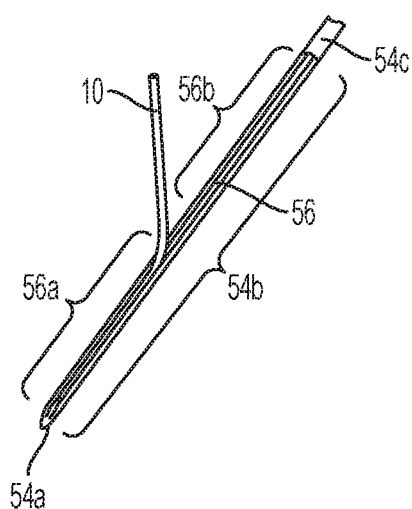
FIG. 15 is a partial perspective view of a slotted needle of the example insertion set device of FIG. 10.
Figure 16:
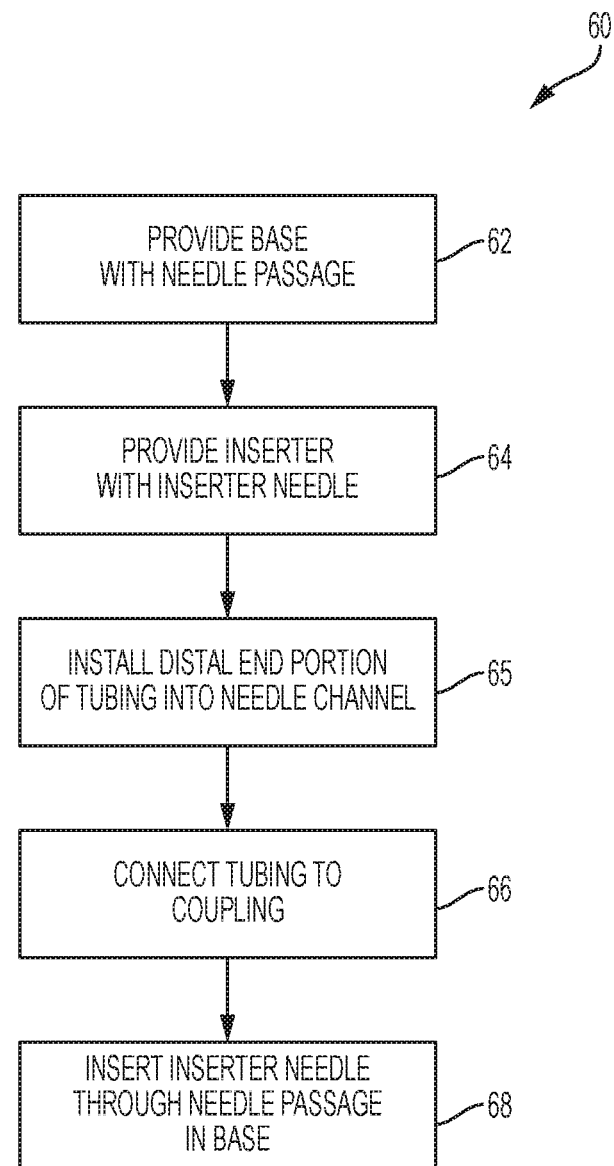
FIG. 16 is a flow chart of a process for making an insertion set device.

The inserter needle 54 has one end that is fixed in or to the inserter body 53, and extends in the axial dimension direction A of the needle, from the inserter body 53 to an opposite, distal end 54a. The distal end 54a of the inserter needle 54 may have a sharp or tapered shape. The inserter needle 54 has a central channel that is open at the distal end 54a, and a slot-shaped opening 56 into the central channel, extending from the distal end 54a, along at least a portion of its axial length. In some examples, the slot-shaped opening 56 extends the entire length of the inserter needle 54. In other examples, as shown in FIG. 15, the slot-shaped opening extends from the distal end 54a, along a first portion 54b of the length of the inserter needle 54, to a second portion 54c of the length of the inserter needle 54, where the second portion 54c has a fully cylindrical shape (hollow or solid). The inserter needle 54 may correspond to the inserter needle 20 described with reference to FIGS. 6 and 7. In other examples, the inserter needle 54 may have other suitable slotted configurations for functioning in the manner described herein.

In certain examples, the slot-shaped opening 56 has a first segment 56a with a first slot width, and a second segment 56b with a second slot width that is larger than the first slot width, as shown in FIG. 15. A slotted inserter needle 54 having multiple widths such as shown in FIG. 15 can help simplify manufacturing, assembly or set-up procedures, as described below. In certain contexts such simplifying of procedures may help to reduce costs of manufacture and assembly of the insertion set device 40. In other examples, the slot-shaped opening 56 may have a constant width along its entire length.

The slotted inserter needle 54 may be made of any suitable, rigid material such as, but not limited to, stainless steel or other metal, ceramic, composite material, plastic, or the like. In certain examples, the slotted inserter needle is made of a material that is biologically compatible, for use in contexts in which the inserter needle is to be in contact or connected with a biological entity (such as a human patient or another biological entity). In certain examples, the inserter needle is treated in one or more processes for enhancing biologically compatibility or other compatibility for an intended environment or use, such as, but not limited to cleaning, sterilizing, treating or coating with Heparin or other anticoagulant, an antibiotic, nitric-oxide or other materials, or the like.

The slotted inserter needle 54 is configured to receive a portion of the flexible tubing 10 (including the distal end portion 10b and distal end 10a) within the central channel of the slotted needle, when the insertion set device 40 is in the first state (as shown in FIGS. 10 and 11). In that arrangement, the slotted inserter needle 54 is slideable relative to the flexible tubing 10, in the axial direction A, by moving the inserter 44 in the axial direction, away from the base 42.

When the insertion set device 40 is in the first state (as shown in FIGS. 10 and 11), a distal end portion of the slotted inserter needle 54 may be inserted into a patient's skin (or a septum or other structure), a sufficient distance to place the distal end of the flexible tubing 10 in the patient (or through the septum or other structure). The slotted inserter needle 54 provides additional rigidity to the distal end portion 10b of the flexible tubing 10 during insertion, and can have a pointed or sharp tip to assist in piercing the patient's skin (or septum or other structure) during insertion.

In addition, the surface 46 of the base 42 of the insertion set device 40 may be secured (adhered or otherwise connected) to a surface of the patient's skin (or a septum or other structure), to hold the base 42 onto the patient's skin (or a septum or other structure).

Once the slotted inserter needle 54 containing the distal end portion 10b of the flexible tubing 10 is inserted into (or partially into) the patient's skin (or a septum or other structure), the slotted inserter needle 54 may be slid off of the flexible tubing 10, while leaving the distal end 10a of the flexible tubing 10 in place in the patient (or through the septum or other structure).

In FIG. 12, the insertion set device 40 is shown in transition between the first state (of FIGS. 10 and 11) and the second state (of FIG. 13). In FIG. 12, the inserter 44 has been moved in the axial direction A from the base 42 a sufficient distance to have caused the slotted inserter needle 54 to have slid partially off of the flexible tubing 10. In that arrangement, the slotted inserter needle 54 has slid off of the distal end portion 10b of the flexible tubing 10.

When the insertion set device 40 is in the first state (shown in FIGS. 10 and 11), and as the slotted inserter needle 54 is being slid off of the distal end portion 10b of the flexible tubing 10 (shown in FIG. 12), the second section of the further length portion 10c of the flexible tubing 10 (forming the bend 10d) extends out from the slot-shaped opening 56 in the inserter needle 54. With the flexible tubing 10 extending out of the slot-shaped opening 56, the slotted inserter needle 54 is allowed to move in the axial direction A relative to the flexible tubing 10 along and past the bend 10d in the flexible tubing 10. Accordingly, the slotted inserter needle 54 may slide off of the flexible tubing 10, while the distal end 10a of the flexible tubing 10 remains in place in the patient (or through the septum or other structure) and while the other end of the flexible tubing 10 remains connected to the coupling 48.

Further movement of the inserter 44 in the axial direction A away from the base 42 causes the slotted inserter needle 54 to slide fully off of the flexible tubing 10. In that arrangement, the insertion set device 40 is in its second state, in which the inserter 44 is fully separated and removed from the base, as shown in FIG. 13. In the second state, the base 42 may remain secured to the surface of the patient's skin (or a septum or other structure) and the distal end portion 10b of the flexible tubing 10 forms a cannula through the patient's skin (or a septum or other structure). The inserter 44 may be safely discarded or stored. In other examples, the inserter 44 need not be removed from the base 42 and may be configured to remain coupled to the base 42 (for example, in the position shown in FIG. 12), as the second state of the insertion set device 40.

Either before or after securing the base 42 to the patient's skin (or a septum or other structure), or before or after sliding the slotted inserter needle 54 relative to the flexible tubing 10, the further tubing 52 may be connected in fluid flow communication with the coupling 48, as described above. Accordingly, the insertion set may be connected to provide a fluid flow connection between the distal end 10a of the flexible tubing 10 (within a patient, septum or other structure), and a pump or other fluid delivery device or source, sensor, monitor or other device or system connected to the further tubing 52.

The inserter device 40 may be manufactured and assembled by any suitable manufacturing and assembly processes. An example process 60 in FIG. 16 includes providing a base 42 (at 62) and providing an inserter 44 (at 64). The base 42 and the inserter 44 may be made by molding, machining, extruding, stamping or other suitable manufacturing processes. The coupling 48 may be secured to the base 42 and any other components (such as, but not limited to, additional support structure for the tubing 10 or tube-like structure forming the passage 50) may be formed in or attached to the base 42. The slotted inserter needle 54 may be formed by molding, machining, extruding, stamping or other suitable manufacturing processes, and may be connected to the inserter body 53 as described above.

The process 60 further includes installing the distal end portion 10b of the flexible tubing 10 into the slotted inserter needle (at 65). The distal end portion 10b of the flexible tubing 10 may be installed in the channel of the slotted inserter needle in any suitable matter, including, but not limited to the matter described with reference to FIG. 15. As shown in FIG. 15, the flexible tubing 10 may be assembled with the slotted inserter needle 54 by inserting the tubing 10 into the inserter needle 54, for example, through the larger width portion 56b of the slot-shaped opening 56, and maintaining or pulling a portion of the length of the tubing out of the larger width portion 56b of the slot-shaped opening 56. Then, the portion of the length of the tubing that has been pulled out of the slot-shaped opening 56 may be gripped and forced in the axial direction A, to pull or push the tubing into the smaller slot-width portion 56a of the inserter needle 54, until the distal end 10a of the flexible tubing 10 is positioned within the smaller slot-width portion 56a of the inserter needle 54 and proximate to the (but not beyond) the distal end 54a of the needle 54.

The end of the length of the tubing portion that has been pulled out of the slot-shaped opening (i.e., the opposite end of the flexible tubing 10 relative to the distal end 10a) is connected to the coupling 48 (at 66). The tubing end may be connected to the coupling 48 in any suitable manner, including, but not limited to inserting the end portion of the flexible tubing into the coupling 48 and adhering the tubing to the coupling 48 as described above.

Prior to or after coupling the flexible tubing 10 to the coupling 48, the slotted insertion needle 54 (with the distal end portion 10b of the tubing) is inserted through the passage 50 (at 68). In other examples, other suitable manufacturing and assembly processes may be employed to form the insertion set device 40.

While the size and dimension of the insertion set device 40 and its components may be selected to accommodate the intended application of use, certain sizes and dimensions may be appropriate for certain medical uses. As one example, an insertion set device 40 may include a flexible tubing 10 having a length L of about 6 mm. (or between about 6 mm and about 9 mm). In addition, the flexible tubing 10 may have an outer radius R of about 0.0045 in. (or about 0.1143 mm) and an L/R ratio and R/r ratio as described above in Table 1, to inhibit kinking or buckling along its length dimension. The inserter needle 54 may have a gauge of 27G, or from 26G to 30G, or an outer radius $R_N$ of about 0.0142 in. (or 0.361 mm) or from 0.01 in. to 0.0159 in. (or 0.25 mm to 0.404 mm.). The inserter needle 54 may have a first slot width in the smaller width portion 56a of about 0.007 in. (or 0.18 mm.), a second slot width in the larger width portion 56b of about 0.0095 in. (or 0.24 mm.), and a length dimension large enough to receive the full length of the distal end portion 10b of the tubing, and to extend through the base and either into or through the inserter. In certain examples, when the insertion set device is in the first state (with the distal end portion 10b of the tubing located within the inserter needle), the minimum distance between the distal end 10a of the tubing 10 to the start of the needle bevel or taper (of the sharp end of the needle) is about 0.020 inch (or 0.508 mm), to avoid or prevent the distal end 10a of the tubing 10 from catching on tissue during insertion. The bevel or taper of the sharp end of the inserter needle 54 may have any suitable length along the length dimension of the inserter needle 54, such as, but not limited to about 0.040 inch (or 1.016 mm), to reduce or minimize patient trauma during insertion. In other examples, the tubing and inserter needle may have other suitable dimensions.

Another example of an insertion set device 70 having a cannula formed with or of a flexible tubing 10 (or other suitable tubing) is described with reference to FIGS. 17-21. The insertion set device 70 is shown in cross-section view in FIG. 17 (corresponding to the cross-section 10-10 in FIG. 11). FIG. 18 shows an enlarged view of a portion of FIG. 17 identified by the circle labeled 18 in FIG. 17.

The insertion set device 70 may be made and may operate and function as described above with respect to the insertion set device 40, with certain differences discussed below. The insertion set device 70 has a base 72 and an inserter 74, which may correspond in structure and function to the base 42 and inserter 44, respectively, as discussed above, with certain differences discussed below.

The inserter 74 has a slotted inserter needle 75, which may correspond to the slotted inserter needle 54 described above. However, the slotted inserter needle 75 may include a slot having a constant width along its length (and need not include two different slot widths, as described with respect to the slotted inserter needle 54 shown in FIG. 15). The slotted inserter needle 75 has a distal end 75a corresponding to the distal end 54a of the slotted inserter needle 54.

In the insertion set device 70, the flexible tubing 10 includes a distal end 10a and distal end portion 10b, as discussed above. The distal end 10a and a distal length portion 10b of the tubing 10 extends out from a first opening 72a in a surface 76 of the base 72. The first opening 72a and surface 76 may correspond to the first opening 42a and surface 46 of the insertion set device 40 discussed above.

A further length portion 10c of the tubing 10 is located within the base 72 and extends from the distal length portion 10b, to a chamber 78 within the base 72. The further length portion 10c of the tubing 10 has an end (opposite to the distal end 10a) that is open to and in fluid flow communication with the chamber 78. The chamber 78 is located in axial alignment with the tubing 10 and the slotted inserter needle 75. Accordingly, the entire length of the tubing 10 in the insertion set device 70 may be normally straight (and need not include a bend 10d as in the inserter set device 40). However, the distal end portion 10b of the tubing 10 may be flexible when the inserter needle 75 is withdrawn.

The chamber 78 may be a sealed interior volume within the base 72, through which fluid may flow and change flow direction, as described herein. The chamber 78 may be formed directly within the material of the base 72. In other examples, the chamber 78 may be the interior of a container structure located and fixed within the base 72.

The base 72 has a first needle passage 80 (corresponding to the passage 50 in the insertion set device 40), that extends, linearly, from the opening 72a to the chamber 78. The base 72 also includes a first septum 82, located between the chamber 78 and a second opening 72b in the base 72. The second opening 72b may correspond to the second opening 42b in the insertion set device 40. The first septum 82 is made of a material suitable to be pierced through by the slotted inserter needle 75, and may be a self-sealing septum material, such as, but not limited to silicon, other rubber material, or the like.

Figure 17:
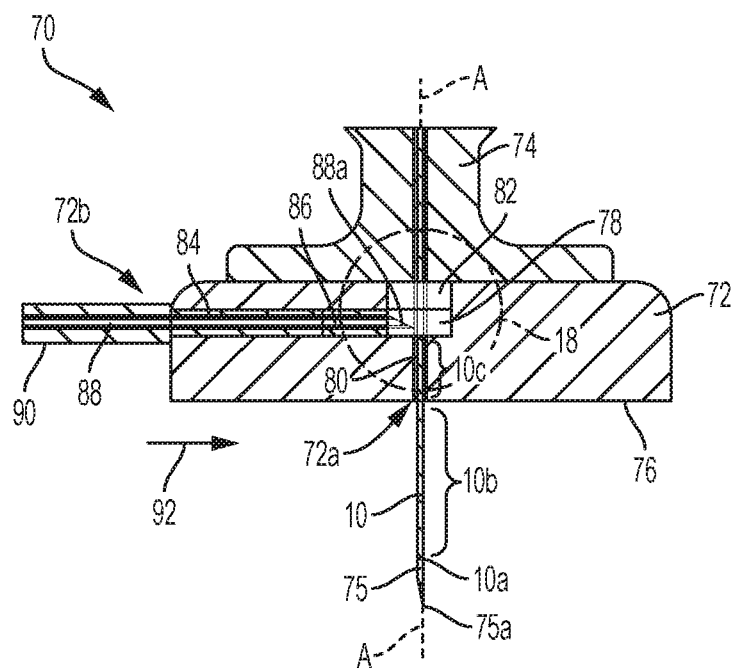
FIG. 17 is a cross-section view of another example insertion set device in a first state.
Figures 18, 19:
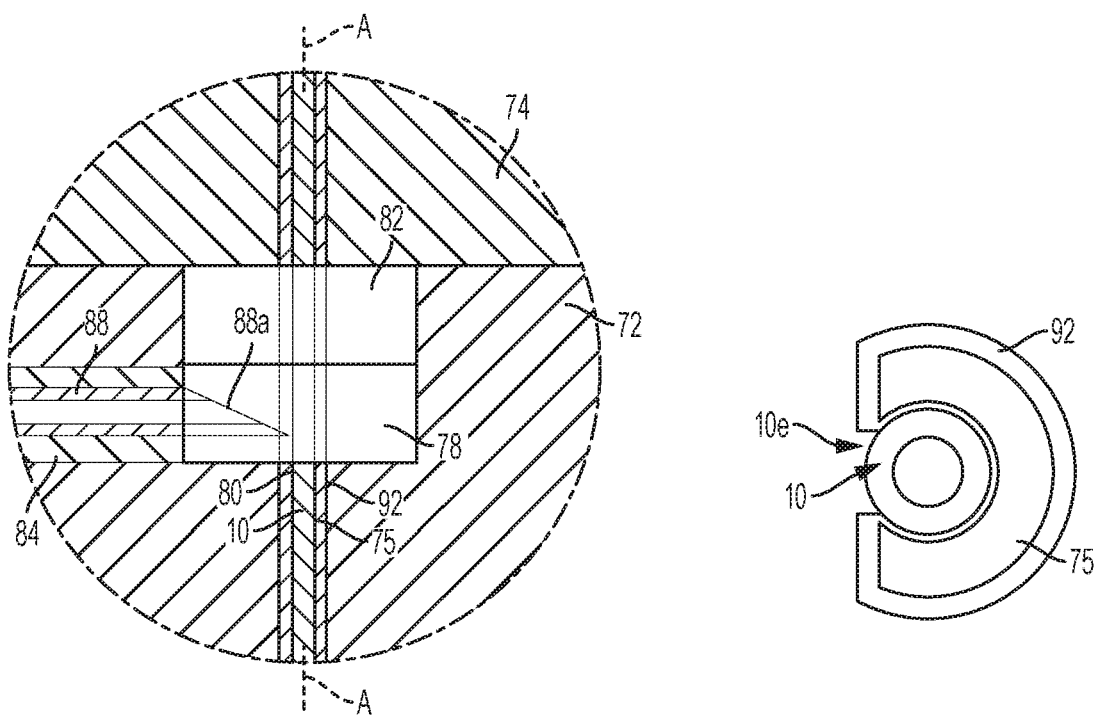
FIG. 18 shows an enlarged view of a portion of FIG. 17 identified by the circle labeled 18 in FIG. 17.
FIG. 19 is a cross-section view of the flexible tubing, the slotted inserter needle and the collar of the example insertion set device of FIG. 17, taken perpendicular to the axial dimension A.

When the insertion set device 70 is in a first state, as shown in FIG. 17, the slotted inserter needle 75 is extended through the first septum 82, the chamber 78 and the needle passage 80. In addition, when the insertion set device 70 is in a first state, as shown in FIG. 17, the flexible tubing 10 (including the distal end 10a) is located within the central channel of the slotted inserter needle 75, and a distal end 75a of the slotted inserter needle 75 is located beyond the distal end 10a of the flexible tubing 10.

The base 72 includes a second needle passage 84 extending linearly and transverse to the axial dimension A and, thus, transverse to the direction of first needle passage 80 and the flexible tubing 10. In certain examples, the second needle passage 84 extends perpendicular to the axial dimension A. In other examples, the second needle passage 84 extends at an angle between about 90° and about 160° (or, in particular examples, between about 135° and about) 160°) relative to the axial dimension A. The second needle passage 84 may be formed directly within the material of the base 72 (such as, by boring, molding or otherwise forming a channel through the material of the base). In other examples, the second needle passage 84 may be the interior of a tube structure included in and fixed to the base 72. The second needle passage 84 has an open end 84a, opening to the exterior of the base 72.

A second septum 86 is located in the second needle passage 84, or between the second needle passage 84 and the chamber 78. The second septum 86 is made of a material suitable to be pierced through by a further needle 88, and may be a self-sealing septum material, such as, but not limited to materials as described above with respect to the first septum 82. The further needle 88 may be a hollow needle for coupling a further tubing 90 in fluid flow communication with the chamber 78 in the base 72. The further tubing 90 may correspond to the further tubing 52 connected to the insertion set device 40, and may connect the insertion set device 70 to other devices and systems as described herein with respect to the further tubing 52.

As shown in FIG. 17, the further needle 88 extends through the second needle passage 84 and through the second septum 86. The further needle 88 has a first end (such as a sharp or pointed end) 88a, located within the chamber 78, and a second end 88b, located in the further tubing 90. The further tubing 90 may be coupled and sealed to the further tubing 90, and has a central passage providing a fluid flow path between the further tubing 90 and the chamber 78 in the base 72.

In particular examples, the further needle 88 and the second septum 86 provide a connector structure that allows the further tubing 90 to be selectively connected or disconnected from the base 72. For example, the further needle 88 may be moved from a position in which the distal end 88a of the further needle 88 is fully outside of the second needle passage 84, to a connected position shown in FIG. 17, by moving the needle 88 through the second needle passage 84 in the direction of arrow 92, until the distal end 88a of the needle 88 pierces through the second septum 86 and is located within the chamber 78. From that position, the further needle 88 may be withdrawn from the second septum 86 and from the base 72, by moving the needle 88 along the second needle passage 84, in a direction opposite to the direction of arrow 92, to selectively disconnect the further tubing 90 from the chamber 78 and from the base 72. Other examples may have other suitable coupling structures for coupling the further tubing 90 to the chamber 78 and the base 72, including but not limited to the coupling devices described above with respect to coupling 48.

In the insertion set device 70, one or more additional features may be provided to hold the flexible tubing 10 within the first needle passage 80, in a fixed relation to the base 72. In certain examples, a collar structure 92 may be provided within the first needle passage 80, to hold the flexible tubing 10 in a fixed relation to the base 72. The collar structure 92 may be adhered to the flexible tubing 10 and to the base 72 by any suitable mechanism, including but not limited to friction fitting, adhesives, welds, or the like.

The collar structure 92 may be made of a material suitable to be pierced through by the slotted inserter needle 75, and may be a self-sealing septum material, such as, but not limited to materials as described above with respect to the first septum 82. When the insertion set device 70 is in the first state shown in FIG. 17, the slotted inserter needle 75 is pierced through the collar structure 92 and contains the flexible tubing 10 within its central channel, as shown in the cross-section drawing of FIG. 19 (taken perpendicular to the axial dimension A, within the base 72, below the chamber 78). In certain examples, the collar structure 92 may extend around some, but not the entire circumference of the tubing 10, without covering a surface portion 10e of the tubing 10 that is exposed through the slot shaped opening of the inserter needle 75, as shown in FIG. 19. In certain examples, additional adhesive material, welding or the like may be provided along the surface 10e of the flexible tubing 10, to adhere the surface 10e of the tubing 10 to the base 72. The collar structure 92 or the additional adhesive or welding retains and holds the flexible tubing 10 to the base 72, as and after the slotted inserter needle 75 is withdrawn and slid off of the flexible tubing 10. In other examples, other suitable structure may be provided for fixing the flexible tubing 10 to the base 72.

Figure 20:
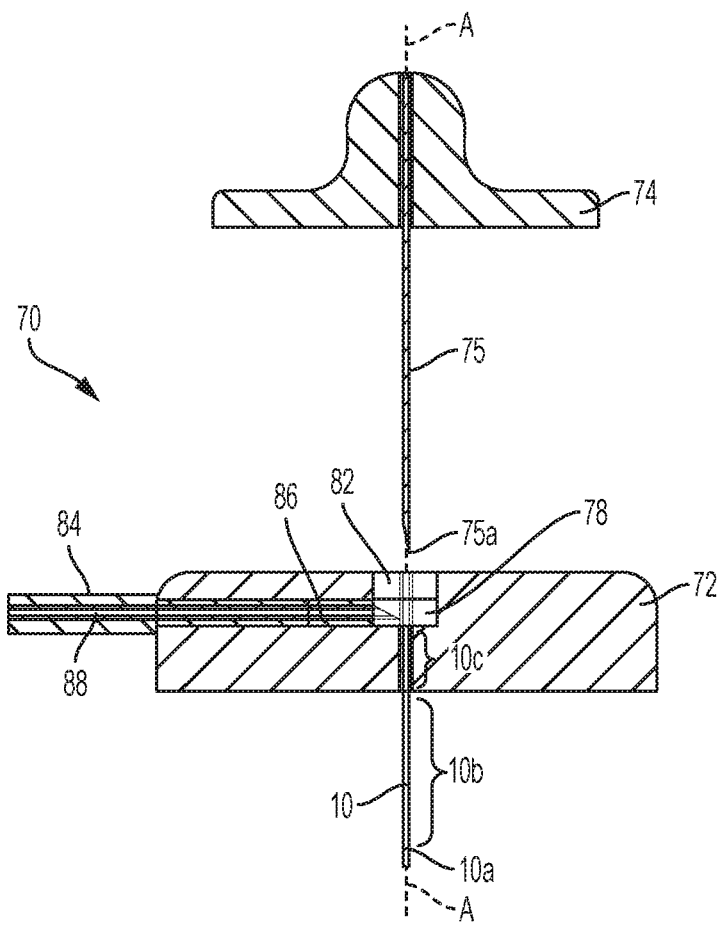
FIG. 20 is a cross-section view the example insertion set device of FIG. 17, in a second state.
Figure 21:
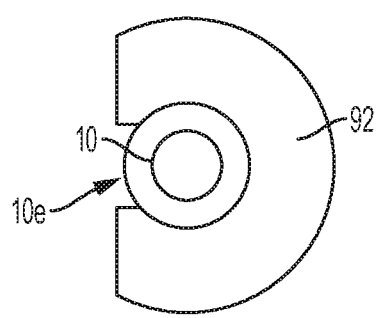
FIG. 21 is a cross-section view of the flexible tubing, the slotted inserter needle and the collar of the example insertion set device of FIG. 20, taken perpendicular to the axial dimension A
Figure 22:
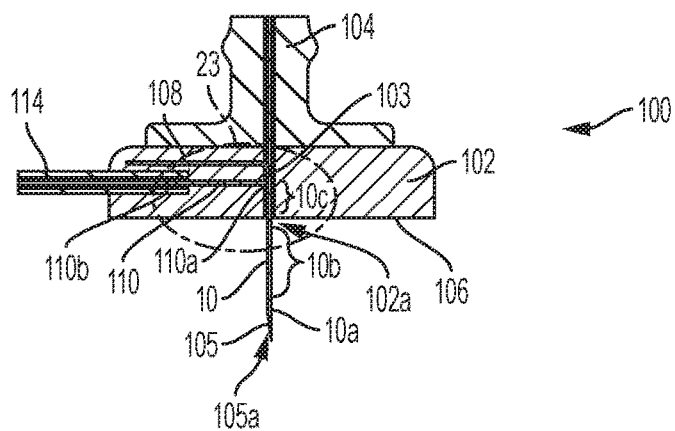
FIG. 22 is a cross-section view of another example insertion set device in a first state.

The insertion set device 70 is shown in FIGS. 20 and 21, in a second state, in which the inserter 74 (including the slotted inserter needle 75) has been fully withdrawn from the base 72. The drawing in FIG. 21 shows the cross-section view of FIG. 19, but with the slotted inserter needle 75 removed from the collar structure 92, where the collar structure 92 is made of a self-sealing material that has sealed after removal of the needle 75.

Figure 23:
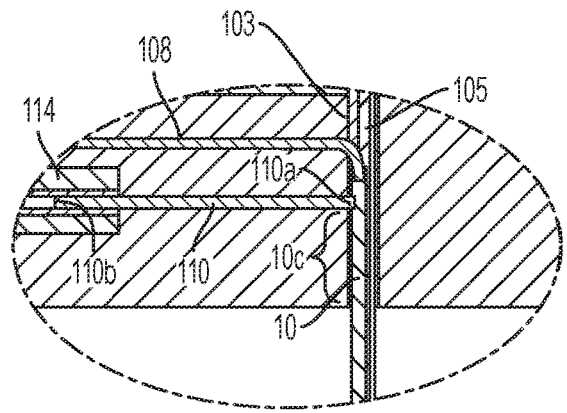
FIG. 23 shows an enlarged view of a portion of FIG. 22 identified by the circle labeled 23 in FIG. 22.
Figure 24:
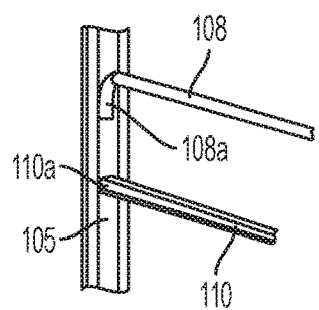
FIG. 24 shows another enlarged view of features in FIG. 23.
Figure 25:
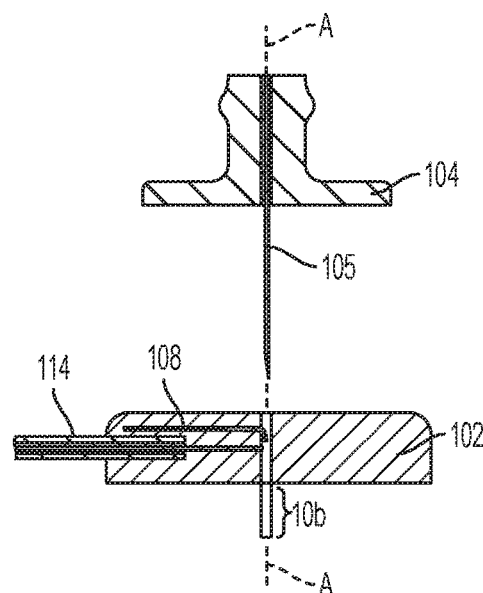
FIG. 25 is a cross-section view the example insertion set device of FIG. 22, in a second state.

Another example of an insertion set device 100 having a cannula formed with or of a flexible tubing 10 (or other suitable tubing) is described with reference to FIGS. 22-25. In FIGS. 23 and 25, the insertion set device 100 is shown in cross-section views (corresponding to the cross-section 10-10 in FIG. 11), in the first state and the second state, respectively. FIG. 23 shows an enlarged view of a portion of FIG. 22 identified by the circle labeled 23, and FIG. 24 shows a further enlarged view of features of the insertion set device 100.

The insertion set device 100 may be made and may operate and function as described above with respect to the insertion set devices 40 and 70, with certain differences discussed below. The insertion set device 100 has a base 102 and an inserter 104, which may correspond in structure and function to the base 42 (or base 72) and inserter 44 (or inserter 74), respectively, as discussed above, with certain differences discussed below. The base 102 includes a needle passage 103 (corresponding to the needle passage 50 in the insertion set device 40).

The inserter 104 has a slotted inserter needle 105, which may correspond to the slotted inserter needle 54 (or 75) described above. However, the slotted inserter needle 105 may include a slot having a constant width along its length (and need not include two different slot widths, as described with respect to the slotted inserter needle 54 shown in FIG. 15). The slotted inserter needle 105 has a distal end 105a corresponding to the distal end 54a (or 75a) of the slotted inserter needle 54 (or 75).

In the insertion set device 100, the flexible tubing 10 includes a distal end 10a and distal end portion 10b, as discussed above. The distal end 10a and a distal length portion 10b of the tubing 10 extends out from a first opening 102a in a surface 106 of the base 102. The first opening 102a and surface 106 may correspond to the first opening 42a and the surface 46 of the insertion set device 40 discussed above (or the first opening 72a and the surface 76 of the insertion set device 70 discussed above).

A further length portion 10c of the tubing 10 is located within the needle passage 103 in the base 102 and extends from the distal length portion 10b, to a holding pin that may be a rigid wire or stop structure 108 within the base 102. The further length portion 10c of the tubing 10 has an end (opposite to the distal end 10a) that is abutted against the rigid wire or stop structure 108. In the example of FIG. 23, the rigid wire or stop structure 108 has an elongated wire or shaft shape with a distal end portion 108a and a bent portion 108b adjacent the distal end portion 108a. The distal end portion 108a may extend partially into the second end of the tubing 10 opposite to the distal end 10a. Alternatively, the distal end portion 108a may contact the end of the tubing 10, without extending into the tubing 10.

The rigid wire or stop structure 108 has a length section that extends within the base 102, and is fixed to the base 102. The rigid wire or stop structure 108 may be molded into the base, or may be fixed to the base 102 by any other suitable mechanism, including but not limited to friction fitting, adhesives, welds, or the like. The rigid wire or stop structure 108 holds and retains the flexible tubing 10 in the base and keeps the flexible tubing 10 from moving with the slotted inserter needle 105, as the slotted inserter needle 105 is withdrawn from the base 102. The bent portion 108b of the rigid wire or stop structure 108 extends out from the slot-shaped opening in the slotted inserter needle 105, when the insertion set device 100 is in the first state shown in FIG. 22, and as the slotted inserter needle 105 is being withdrawn from the base 102.

The base 102 includes a hollow tube structure 110 having a first end 110a connected in fluid flow communication with the further length portion 10c of the tubing 10. In one example, the end 110a of the tube structure 110 is inserted partially into the side of the further length portion 10c of the flexible tubing 10. The tube structure 110 extends through the slot-shaped opening in the slotted inserter needle 105, when the insertion set device 100 is in the first state shown in FIG. 22, and as the slotted inserter needle 105 is being withdrawn from the base 102. The tube structure 110 provides a fluid flow passage to or from the flexible tubing 10. In certain examples, the tube structure 110 may have an oval or widened cross-section shape (as shown in the further view of FIG. 24), to provide a greater fluid flow volume, relative to a tube structure having a round cross-section that would fit through the slot-shaped opening in the slotted inserter needle 105.

The hollow tube structure 110 may have a second end 110b connected in fluid flow communication with a coupling 112. The coupling 112 may correspond to the coupling 48 of the insertion set device 40, or another suitable fluid coupling device, for coupling a further tubing 114 to the base 102, in fluid flow communication with the tube structure 110. The further tubing 114 may correspond to the further tubing 52 or the further tubing 90 discussed above.

The hollow tube structure 110 extends from the further length portion 10c of the tubing 10 to the coupling 112. The length dimension of the hollow tube structure 110 may extend linearly and transverse to axial dimension A of the tubing 10, such that the height H in the axial dimension of the base 102 (dimension between the surface 106 and the opposite facing surface) may be made relatively small or minimized. In certain examples, the hollow tube structure 110 extends at about 90° relative to the axial dimension, such that the coupling 112 is directed about 90° from the direction of distal length portion 10b of the tubing 10. This arrangement allows the further tubing 114 to be connected to the coupling 112, external to the base 102, and extend outward from the base 102, substantially parallel to and along the surface of the patient's skin (or other surface) to which the base 102 secures. Accordingly, the base 102 and tubing 10 may be more easily concealed under clothing or the like. In other examples, the hollow tube structure 110 may extend at an angle between about 90° and about 160° (or, in particular examples, between about 135° and about 160°), relative to the axial dimension A.

Another example of an insertion set device 120 having a cannula formed with or of a flexible tubing 10 (or other suitable tubing) is described with reference to FIGS. 26-29. In FIGS. 26 and 29, the insertion set device 120 is shown in cross-section views (corresponding to the cross-section 10-10 in FIG. 11), in the first state and the second state, respectively. FIG. 27 shows an enlarged view of a portion of FIG. 26 identified by the circle labeled 27 in FIG. 26, and FIG. 28 shows a further enlarged view of features of the insertion set device 120.

The insertion set device 120 may be made and may operate and function as described above with respect to the insertion set device 100, with certain differences discussed below. The insertion set device 120 has a base 122 and an inserter 124, which may correspond in structure and function to the base 102 (or bases 42 or 72) and inserter 104 (or inserters 44 or 74), respectively, as discussed above, with certain differences discussed below. The base 122 includes a needle passage 123 (corresponding to the needle passage 103 in the insertion set device 100).

The inserter 124 has a slotted inserter needle 125, which may correspond to the slotted inserter needle 105 (or 54 or 75) described above. The slotted inserter needle 125 may include a slot having a constant width along its length (and need not include two different slot widths, as described with respect to the slotted inserter needle 54 shown in FIG. 15). The slotted inserter needle 125 has a distal end 125a corresponding to the distal end 105a (or 54a or 75a) of the slotted inserter needle 105 (or 54 or 75).

In the insertion set device 120, the flexible tubing 10 includes a distal end 10a and distal end portion 10b, as discussed above. The distal end 10a and a distal length portion 10b of the tubing 10 extends out from a first opening 122a in a surface 126 of the base 122. The first opening 122a and surface 126 may correspond to the first opening 102a and the surface 126 of the insertion set device 100.

A further length portion 10c of the tubing 10 is located within the needle passage 123 in the base 122 and extends from the distal length portion 10b, to a rigid, hollow tube 128 within the base 122. The further length portion 10c of the tubing 10 has an end (opposite to the distal end 10a) that is abutted against the rigid tube 128. In the example of FIG. 26, the rigid tube 128 has an elongated tubular shape with a distal end portion 128a and a bent portion 128b adjacent the distal end portion 128a. The distal end portion 128a may extend partially into the second end of the tubing 10 opposite to the distal end 10a. Alternatively, the distal end portion 128a may connect to the end of the tubing 10 through a fluid flow connector, without extending into the tubing 10.

The hollow, rigid tube 128 has a length section that extends within the base 122 (between the bent portion 128b and a second end 128c), and is fixed to the base 122. The rigid tube 128 may be molded into the base 122, or may be fixed to the base 122 by any other suitable mechanism, including but not limited to friction fitting, adhesives, welds, or the like. The rigid tube 128 holds and retains the flexible tubing 10 in the base and keeps the flexible tubing 10 from moving with the slotted inserter needle 125, as the slotted inserter needle 125 is withdrawn from the base 122. The bent portion 128b of the rigid tube 128 extends out from the slot-shaped opening in the slotted inserter needle 125, when the insertion set device 120 is in the first state shown in FIG. 26, and as the slotted inserter needle 125 is being withdrawn from the base 122.

The hollow, rigid tube 128 has a fluid flow channel that provides a fluid flow path between the tubing 10 and a further tubing 130. The further tubing 130 may correspond to the further tubing 114, 90 or 52 discussed above. The further tubing 130 may be connected in fluid flow communication with a second end 128c of the hollow, rigid tube 128 (opposite to the distal end portion 128a) within the base 122 (as shown in FIGS. 26 and 29), or outside of the base 122. For example, a portion of the hollow, rigid tube 128 and the second end 128c may extend into the further tubing 130 and be sealed and adhered to the further tubing 130 by any suitable mechanism, including, but not limited to adhesives, welding, or the like. Alternatively, the hollow, rigid tube 128 may be connected in fluid flow communication with the further tubing through any suitable in-line or other fluid flow coupling device, such as, but not limited to a Luer Lok™ device, Luer™-slip device, slip tip device, hollow needle and septum configuration or the like.

The hollow, rigid tube 128 may have a round cross-section shape (taken perpendicular to its length dimension), and may be made of any suitable, rigid material such as, but not limited to stainless steel or other metal, plastic, ceramic, composite material, or the like. The hollow, rigid tube 128 may be made by any suitable manufacturing process including, but not limited to molding, machining, extruding, stamping or other the like.

The hollow, rigid tube 128 has a length section 128d that extends within the base 122 between the bent portion 128b and a second end 128c. Due to the bent portion 128b, the length section 128d of the hollow, rigid tube 128 may extend linearly and transverse to axial dimension A of the tubing 10, such that the height H in the axial dimension of the base 122 (dimension between the surface 106 and the opposite facing surface) may be made relatively small or minimized. In certain examples, the length section 128d of the hollow, rigid tube 128 extends at about 90° relative to the axial dimension. This arrangement allows the further tubing 130 to be connected and extend outward from the base 122, substantially parallel to and along the surface of the patient's skin (or other surface) to which the base 122 secures. Accordingly, the base 122 and tubing 10 may be more easily concealed under clothing or the like. In other examples, the length section 128d of the hollow, rigid tube 128 may extend at an angle between about 90° and about 160° (or, in particular examples, between about 135° and about 160°), relative to the axial dimension A.

Figure 30:
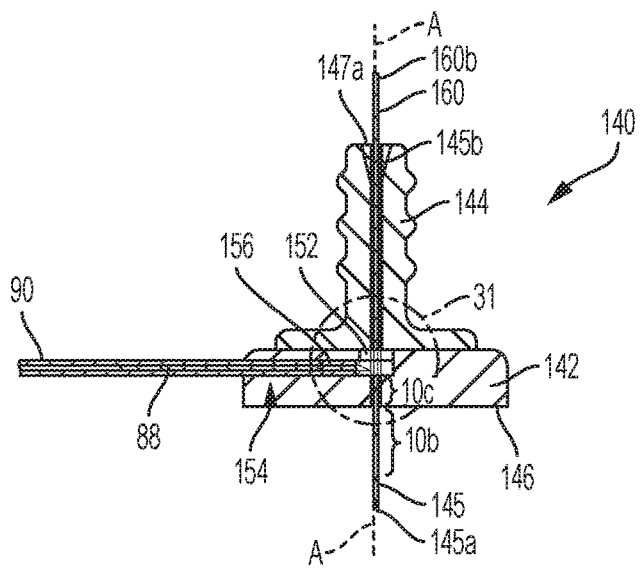
FIG. 30 is a cross-section view of another example insertion set device in a first state.
Figure 31:
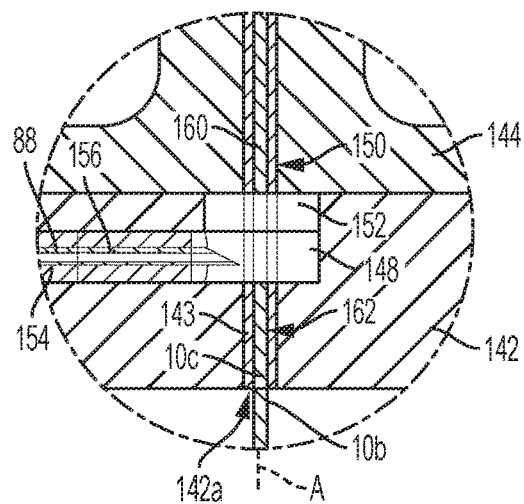
FIG. 31 shows an enlarged view of a portion of FIG. 30 identified by the circle labeled 31 in FIG. 30.
Figure 32:
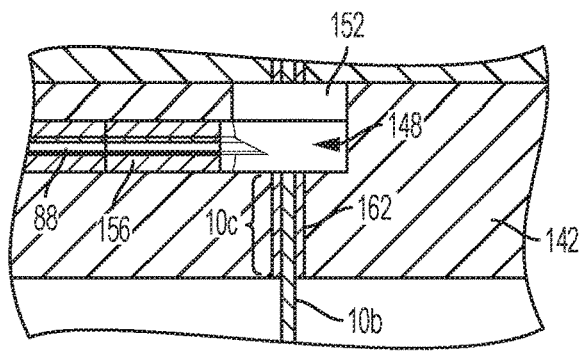
FIG. 32 shows another enlarged view of features in FIG. 31, in a second state.

Another example of an insertion set device 140 having a cannula formed with or of a flexible tubing 10 (or other suitable tubing) is described with reference to FIGS. 30-32. In FIG. 30, the insertion set device 140 is shown in a cross-section view (corresponding to the cross-section 10-10 in FIG. 11), in the first state. FIG. 31 shows an enlarged view of a portion of FIG. 30 identified by the circle labeled 31, and FIG. 32 shows a further enlarged view of features of the insertion set device 140.

The insertion set device 140 may be made and may operate and function as described above with respect to the insertion set device 70, with certain differences discussed below. The insertion set device 140 has a base 142 and an inserter 144, which may correspond in structure and function to the base 72 and inserter 74, respectively, as discussed above, with certain differences discussed below. The base 142 includes a needle passage 143 (corresponding to the needle passage 80 in the insertion set device 70).

In the insertion set device 140, the flexible tubing 10 includes a distal end 10a and distal end portion 10b, as discussed above. The distal end 10a and a distal length portion 10b of the tubing 10 extends out from a first opening 142a in a surface 146 of the base 142. The first opening 142a and surface 146 may correspond to the first opening 72a and the surface 76 of the insertion set device 70. A further length portion 10c of the tubing 10 is located within the needle passage 143 in the base 142 and extends from the distal length portion 10b, to a chamber 148 (corresponding to the chamber 78 in the insertion set device 70). The insertion set device 140 also includes a first septum 152, a second needle passage 154 and a second septum 156 (corresponding to the first septum 82, the second needle passage 84 and the second septum 86 in the insertion set device 70). In addition, the insertion set device 140 may be configured to connect with a further needle 88 and a further tubing 90, as discussed above with respect to the insertion set device 70.

The inserter 144 has a hollow inserter needle 145 that has a central channel extending along its entire length. In some examples, the inserter needle 145 may correspond to the slotted inserter needle 75 described above. However, in other examples, the inserter needle 145 need not be slotted and, instead, may have a hollow, fully round cylindrical configuration. In addition, the inserter needle 145 is configured to be received by and selectively removable from a body portion 147 of the inserter 144. The body portion 147 of the inserter 144 may correspond to the body portion of the inserter 74 (and the inserter body 53) described above, but includes a needle passage 150 extending linearly through the body portion 147. The needle passage 150 is arranged to be in linear alignment with the needle passage 143 in the base 142 and is coaxial with the axis A of the tubing 10, when the insertion set device 140 is in the first state as shown in FIG. 30.

The insertion set device 140 also includes a removable holding pin 160 having a first end 160a and an opposite second end 160b. When the insertion set device 140 is in the first state (as shown in FIGS. 30 and 31), the holding pin 160 is received within, and extends along a portion of the length of the hollow inserter needle 145, but is removable from the hollow inserter needle 145 by sliding out of the channel of the needle 145, along a direction of the axis A.

In that first state, the tubing 10 is also received with and extends along another portion of the length of the hollow inserter needle 145. The holding first end 160a of the holding pin 160 is arranged to abut the second end of the tubing 10 (opposite to the distal end 10a), within the channel of the hollow inserter needle 145, while the second end 160b of the holding pin 160 is exposed (for example, by extending out from an opening 147a in the inserter body portion 147) at an end of the needle passage 150. In certain examples, the holding pin 160 may extend partially into the second end of the tubing 10. In other examples, the holding pin 160 contacts, but does not enter the tubing 10. The opening 147a in the inserter body portion 147 may be flared so as to taper wider from the width of the needle passage 150 to a wider width at the open end of the opening 147a, for easier access to the hollow inserter needle 145.

The insertion set device 140 may include a collar structure 162 within the needle passage 143 and around the length portion 10c of the tubing 10, to help retain the tubing 10 within and fixed to the base 142, when the inserter needle 145 and the holding pin 160 are removed. The collar structure 162 may be made of a material suitable to be pierced through by the hollow inserter needle 145, and may be a self-sealing septum material, such as, but not limited to materials as described above with respect to the collar structure 92 described above. The collar structure 162 may be adhered to the flexible tubing 10 and to the base 142 by any suitable mechanism, including but not limited to friction fitting, adhesives, welds, or the like.

When the insertion set device 140 is arranged in the first state (as shown in FIGS. 30 and 31), the entire length of the tubing 10 and a portion of the length of the holding pin 160 are received within the channel of the hollow inserter needle 145. In addition, the holding pin 160 abuts the tubing 10, to retain and hold the tubing 10 from moving with the hollow inserter needle 145, when the hollow inserter needle 145 is being withdrawn.

In that first state, the insertion set device 140 may be inserted or installed on a patient, septum or other device, and the further tubing 90 may be connected to the base 142 (similar to the manner of installing devices in examples of FIGS. 10-29, as described above)

After insertion or installation of the insertion set device 140, the hollow inserter needle 145 is withdrawn from the base 142 and inserter 144, by moving the hollow needle in the direction of the axis A, away from the inserter 144. For example, a user (or tool or machine) may grip the hollow inserter needle 145 near the end 145b, and may pull the hollow inserter needle 145 outward (upward in FIG. 30) along the direction of the axis A of the needle passages 143 and 150 and of the tubing 10, to withdraw the hollow needle from the base 142 and the inserter 144. At the same time, the holding pin 160 remains abutted with the tubing 10, to retain the tubing 10 within the base 142, and keep the tubing 10 from moving with the hollow inserter needle 145, as the inserter needle is withdrawn.

Once the hollow inserter needle 145 has been fully withdrawn, the holding pin 160 may be withdrawn by moving the holding pin 160 in the direction of the axis A, away from the inserter 144. For example, a user (or tool or machine) may grip the holding pin 160, near the exposed second end 160b, and may pull the holding pin 160 outward (upward in FIG. 30) along the direction of the axis A of the needle passage 150, away from the tubing 10, to withdraw the holding pin 160 from the base 142 and the inserter 144. At the same time, the tubing 10 remains retained within and fixed to the base 142, by the collar structure 162. Accordingly, the insertion set device 140 is transitioned to the second state (as shown in FIG. 32), after the inserter needle 145 and the holding pin 160 have been withdrawn.

While various exemplary embodiments have been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

We claim:

1. A medical device comprising a fluid flow tubing configured to resist kinking, the tubing having a length L extending along an axial dimension of the tubing, the tubing having a fluid flow passage, a needle having a channel extending from a distal end of the needle along at least a portion of an axial length dimension of the needle, and a base, wherein the fluid flow tubing is located at least partially within the channel of the needle, wherein the needle has a side slot extending along a generally linear section of the needle in a direction of the axial length dimension of the needle and open to the channel, wherein a portion of the fluid flow tubing including a portion of the fluid flow passage extends out of the channel through the side slot, the fluid flow tubing having a distal end located within the channel of the needle and a second end located outside of the channel of the needle, the needle being slideable in the axial dimension relative to the fluid flow tubing, to selectively slide off of the distal end of the fluid flow tubing, wherein at least some of the portion of the fluid flow tubing extending outside of the channel is held by the base in a fixed position relative to distal end of the fluid flow tubing to inhibit movement of the tubing with the needle as the needle is slid off of the distal end of the fluid flow tubing, and wherein the entire portion of the fluid flow tubing located outside of the channel is contained in the base, in a fixed position relative to the distal end of the fluid flow tubing.

2. The medical device of claim 1, wherein the tubing has an inside radius r and an outside radius R, and wherein R/r is equal to or greater than 1.5.

3. The medical device of claim 1, wherein the tubing has a length L and an outside radius R, and wherein L/R is within the range of 34.889 to 78.667.

4. The medical device of claim 1, wherein the tubing is made of a polyether block amide (PEBA) or other thermoplastic elastomer (TPE).

5. The medical device of claim 1, wherein the fluid flow tubing has a first section including a first portion of the fluid flow passage that is located in the channel of a hollow needle, a second section including a second portion of the fluid flow passage located outside of the channel of the hollow needle, and a further section including the portion of the fluid flow passage that extends through the side slot of the hollow needle, the further section connecting the first portion of the fluid flow passage with the second portion of the fluid flow passage.

6. The medical device of claim 1, wherein: the fluid flow tubing including the portion of the fluid flow passage extends through the side slot of the needle as the needle is slid at least partially off of the fluid flow tubing; and the slot extends from a distal end of the needle, along at least a portion of the axial length dimension of the needle.

7. The medical device of claim 1, wherein the slot extends from the distal end of the needle, along the entire axial length dimension of the needle.

8. The medical device of claim 1, wherein the needle has a "C" shaped cross-section shape taken perpendicular to the axial length dimension of the needle.

9. The medical device of claim 1, wherein the side slot in the needle has a first width along a first section of the axial length dimension of the needle and a second width along a second section of the axial length dimension of the needle, the first width being different than the second width.

10. The medical device of claim 1, wherein the base has at least one of a surface configured to abut and be secured to a patient's skin, and a mechanism for securing the base externally to a patient's skin.

11. The medical device of claim 1, wherein the needle has a circular cross-section shape taken perpendicular to the length dimension, the tubing having a fluid flow passage along the length L, an inside radius r and an outside radius R, wherein L/R is equal to or greater than 34.8.

12. The medical device of claim 11, wherein: L/R is within the range of 34.889 to 78.667; and R/r is equal to or greater than 1.5.

13. The medical device of claim 12, wherein the tubing is made of a polyether block amide (PEBA) or other thermoplastic elastomer (TPE).

14. A method of making a medical device comprising:
providing a kink resistant fluid flow tubing having a length L extending along an axial dimension of the tubing and a fluid flow passage along the length L;
receiving a first portion of the fluid flow tubing within a channel in a needle, the channel extending from a distal end of the needle along at least a portion of a length of the needle, wherein the needle has a side slot extending along a generally linear section of the needle in a direction of the length of the needle and open to the channel; and
extending a second portion of the fluid flow tubing including a portion of the fluid flow passage out of the channel and through the side slot of the needle;
wherein the needle is slideable in the axial dimension relative to the fluid flow tubing, to selectively slide off of at least a distal end portion of the fluid flow tubing;
wherein the method further comprises holding at least some of the second portion of the fluid flow tubing in a fixed position relative to the distal end portion of the fluid flow tubing to inhibit movement of the fluid flow tubing with the needle when the needle is slid off of the distal end portion of the fluid flow tubing; and
wherein the entire portion of the fluid flow tubing located outside of the channel is held in the base, in a fixed position relative to the distal end of the fluid flow tubing.

15. The method of claim 14, wherein the fluid flow tubing has an outside radius R, and wherein L/R is equal to or greater than 34.8.

16. The method of claim 15, wherein the fluid flow tubing has an inside radius r, and wherein R/r is equal to or greater than 1.5.

17. The method of claim 16, wherein providing the kink resistant fluid flow tubing comprises forming the tubing of polyether block amide (PEBA) or other thermoplastic elastomer (TPE).

18. The method of claim 14, wherein the fluid flow tubing has an outside radius R, and wherein L/R is within the range of 34.889 to 78.667.

19. The method of claim 14, wherein providing the kink resistant fluid flow tubing comprises forming a tubing of polyether block amide (PEBA) or other thermoplastic elastomer (TPE).

20. The method of claim 14, further comprising providing the base has at least one mechanism for securing the base externally to a patient's skin.

21. A medical device comprising:
a hollow needle having a central channel, a side slot extending along a generally linear section of the needle in a length dimension of the needle and open to the channel, a distal end and an opening at the distal end;
a fluid flow tubing configured to resist kinking, the tubing having a length L extending along an axial dimension of the tubing, and a circular cross-section shape taken perpendicular to the length dimension, the tubing having a fluid flow passage along the length L and an outside radius R, wherein L/R is equal to or greater than 34.8, the tubing having a distal end and a length portion located within the central channel of the hollow needle, the fluid flow tubing having a portion including a portion of the fluid flow passage that extends out of the channel through the side slot of the needle; and
a base;
wherein the needle is slideable in the axial dimension relative to the tubing, to selectively slide off of at least the distal end of the tubing, and cause the distal end of the tubing to exit the channel through the opening at the distal end of the needle as the needle is slid at least partially off of the tubing, while the portion of the fluid flow tubing including the portion of the fluid flow passage extends out of the channel through the side slot of the needle;
wherein at least a portion of the fluid flow tubing outside of the channel of the needle is held by the base in a fixed position relative to the distal end of the fluid flow tubing to inhibit movement of the fluid flow tubing with the needle as the needle is slid off of the distal end of the fluid flow tubing; and wherein the entire portion of the fluid flow tubing located outside of the channel is contained in the base, in a fixed position relative to the distal end of the fluid flow tubing.

22. A medical device comprising a fluid flow tubing configured to resist kinking, the tubing having a length L extending along an axial dimension of the tubing, the tubing having a fluid flow passage, a needle having a channel extending from a distal end of the needle along at least a portion of an axial length dimension of the needle, and a base, wherein the fluid flow tubing is located at least partially within the channel of the needle, wherein the needle has a side slot extending along a generally linear section of the needle in a direction of the axial length dimension of the needle and open to the channel, wherein a portion of the fluid flow tubing including a portion of the fluid flow passage extends out of the channel through the side slot, the fluid flow tubing having a distal end located within the channel of the needle and a second end located outside of the channel of the needle, the needle being slideable in the axial dimension relative to the fluid flow tubing, to selectively slide off of the distal end of the fluid flow tubing, wherein at least some of the portion of the fluid flow tubing extending outside of the channel is held by the base in a fixed position relative to distal end of the fluid flow tubing to inhibit movement of the tubing with the needle as the needle is slid off of the distal end of the fluid flow tubing, and wherein the portion of the fluid flow tubing extending outside of the channel is held by the base in a fixed bend of between about 90° and about 160°.

* * * * *